(12) United States Patent
LaFauci et al.

(10) Patent No.: US 8,628,934 B2
(45) Date of Patent: Jan. 14, 2014

(54) SYSTEM AND METHOD FOR QUANTIFYING FRAGILE X MENTAL RETARDATION 1 PROTEIN IN TISSUE AND BLOOD SAMPLES

(75) Inventors: Giuseppe LaFauci, Old Bridge, NJ (US); William T. Brown, Staten Island, NY (US); Richard Kascsak, Morganville, NJ (US)

(73) Assignee: The Research Foundation For Mental Hygiene, Inc., Menands, NY (US)

( * ) Notice: Subject to any disclaimer, the term of this patent is extended or adjusted under 35 U.S.C. 154(b) by 0 days.

(21) Appl. No.: 13/493,318

(22) Filed: Jun. 11, 2012

(65) Prior Publication Data

US 2013/0149722 A1  Jun. 13, 2013

Related U.S. Application Data

(60) Provisional application No. 61/495,679, filed on Jun. 10, 2011.

(51) Int. Cl.
 *G01N 33/53* (2006.01)
 *G01N 33/68* (2006.01)

(52) U.S. Cl.
 USPC .............................. 435/7.94; 435/7.1; 436/86

(58) Field of Classification Search
 USPC .................................... 435/7.94, 7.1; 436/86
 See application file for complete search history.

(56) References Cited

U.S. PATENT DOCUMENTS 6,180,337 B1 * 1/2001 Caskey et al. ................ 435/6.12
6,303,770 B1 * 10/2001 Lok et al. .................... 536/23.5

OTHER PUBLICATIONS

Iwahashi, et al., A Quantitative ELISA Assay for the Fragile X Mental Retardation 1 Protein, Journal of Molecular Diagnostics, 11(4), (2009) p. 281-289.*
Harlow, E. and Lane, D., Antibodies: A Laboratory Manual (1988) Cold Spring Harbor Laboratory Press, Cold Spring Harbor, NY, p. 553-612.*
Harlow, E. and Lane, D., Antibodies: A Laboratory Manual (1988) Cold Spring Harbor Laboratory Press, Cold Spring Harbor, NY, p. 59-87, 173-174, 473-480.*

* cited by examiner

*Primary Examiner* — Christine Foster
*Assistant Examiner* — Ellen J Marcsisin
(74) *Attorney, Agent, or Firm* — David L. Nocilly; Bond Schoeneck & King, PLLC

(57) ABSTRACT

A system and method for the detection and quantification of fragile X mental retardation protein (FMRP) in human tissue and blood samples. The system includes several high avidity monoclonal antibodies that may be provided on Xmap microspheres to capture FMRP from a tissue or blood specimen. The resulting complex is reacted with a polyclonal anti-FMRP rabbit antibody and then mixed with an anti-rabbit IgG antibody conjugated to phycoerythrin. Fluorescence emitted from the resulting complex is a function of the amount of FMRP present in the specimen.

4 Claims, 20 Drawing Sheets

FIGURE 14A-C

FIGURES 19A and B

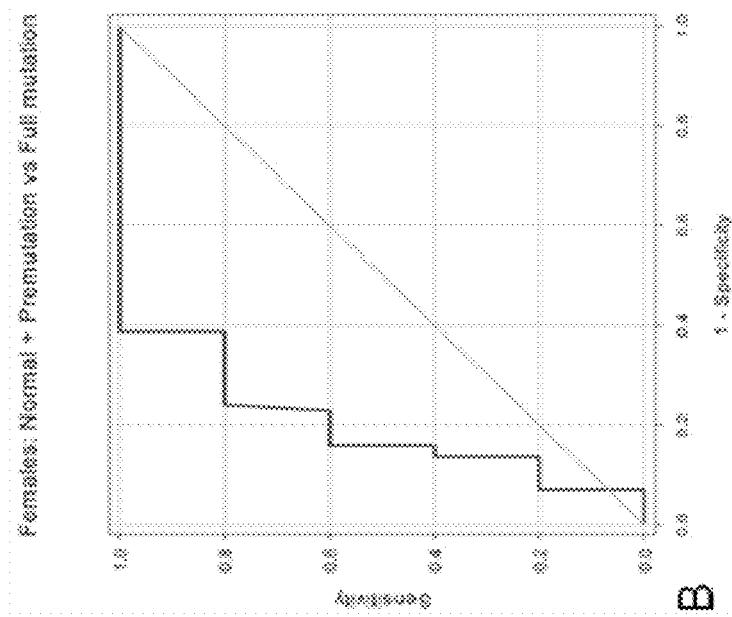
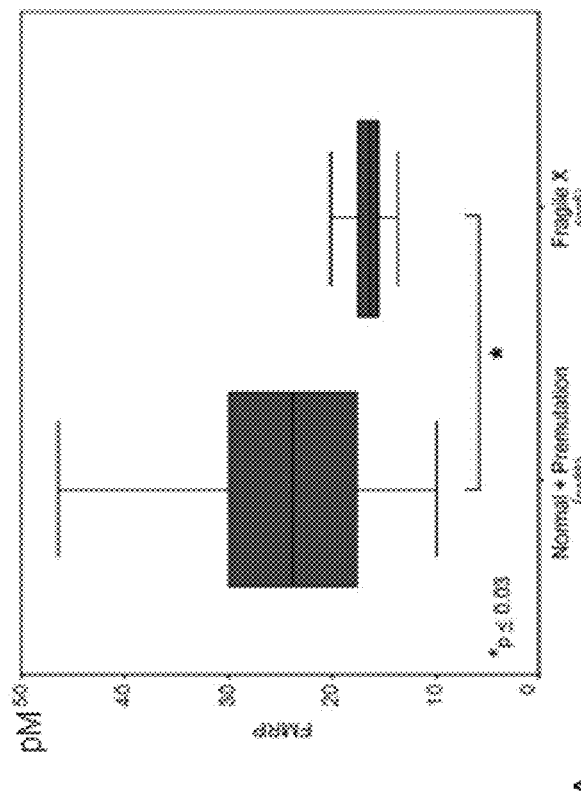
FIGURES 21A and B

SYSTEM AND METHOD FOR QUANTIFYING FRAGILE X MENTAL RETARDATION 1 PROTEIN IN TISSUE AND BLOOD SAMPLES

CROSS-REFERENCE TO RELATED APPLICATIONS

The present application claims priority to U.S. Provisional Application No. 61/495,679, filed on Jun. 10, 2011.

BACKGROUND OF THE INVENTION

1. Field of the Invention

The present invention relates to fragile X mental retardation 1 protein detection and, more specifically, to a system and method for quantifying the protein in tissue samples in a capture immunoassay using anti-FMRP antibodies.

2. Description of the Related Art

Fragile X syndrome (FXS) is a heritable condition characterized by cognitive and behavioral abnormalities and is the most common single gene cause of autism. The syndrome results from an expanded triplet CGG repeat that generates a fragile X site on the X chromosome that results in the absence or reduced expression of the FMR1 gene product FMRP. Almost all individuals with the syndrome carry FMR1 forms (alleles) that do not express the protein because the mutated alleles harbor long stretches of hypermethylated CGG repeats, e.g., the full mutation (FM) has more than 200 CGG repeats, that abolish or compromise FMRI transcription and/or translation. Alleles containing shorter repeats, e.g., permutations of 55 to 200 CGG repeats, may express a reduced amount of FMRP.

Most individuals carrying the permutation (PM) are not cognitively affected. However, PM alleles have been reported to play a role in autism spectrum disorders, premature ovarian failure and fragile X-associated tremor-ataxia syndrome. Early diagnosis of the syndrome is extremely important for child supportive care, early intervention and for family planning.

The laboratory diagnosis of Fragile X syndrome is currently performed by DNA testing (Southern blot and PCR methods) using blood or other tissues. The tests often require several days (7-10 days), however, and can be performed only by a limited number of specialized laboratories. These methods are directed at determining the length of the CGG repeats in the FMR1 alleles and use the CGG repeat size of the allele to infer or predict whether the proband cells produce abnormal levels of FMRP.

The development of an immunoassay for the direct quantification of FMRP has been hampered by the lack of mouse monoclonal antibodies (mAbs) having the affinity required to capture efficiently the human protein while showing no cross reactivity with the Fragile X related proteins, FXR1P and FXR2P. Various attempts have been made to test directly for the presence of FMRP in blood and other tissues using mAb IC3 that recognizes an epitope localized in the N-terminal of FMRP. The problem with these tests, however, is that the 1C3 mAb cross-reacts with the FX related protein FXRI and does not have a strong binding affinity to FMRP.

For example, one test uses a Western blot analysis to study FMRP expression in human lymphocytes from FM patients, PM and normal individuals. This test uses an anti-FMRP mAbla from Chemicon that cross reacts with a 70 kd protein (FXR1) in FM male samples. Immunocytochemical staining of lymphocytes or hair root cells using an anti-FMRP mAb (1C3) has also been used to detect cells expressing FMRP. Cells from male FM patients are not stained or show a small percentage of stained cells. The test does not measure the quantity of FMRP, but instead determines the fraction of cells that express the protein.

Finally, a luminometer-based sandwich ELISA for FMRP that allows quantification of FMRP in lymphocytes within 3 to 4 days has been described in the art. The assay uses a chicken polyclonal Ab to capture FMRP and a commercially available mAb, 1C3 (Chemicon, Millipore) for detection. Because of cross-reacting, this test produces a high background that does not allow signal detection when used with common blocking agents as milk and BSA. While the background may be reduced or suppressed using hydrolyzed casein as blocking agent, the blocking step—usually performed before incubation with the antigen—must follow the incubation with the antigen (lymphocyte extract) in order to produce a detectable signal and the ability of the chicken polyclonal Ab to capture FMRP from the lymphocyte extracts is reduced or abrogated by the presence of the blocking agent. In addition, this ELISA is cumbersome, time consuming (around 3 to 4 days), and requires several long incubation times, such as 24-48 hours for binding of the chicken Ab to the plate, overnight incubation for binding of antigen, about 2 hours for blocking, 8-10 hours for binding with the detecting mAb, and then about 12 hour for binding with horseradish peroxydase-conjugated donkey anti-mouse IgG. Accordingly, there remains a need for an immunoassay that is relatively fast and does not require a specialized laboratory.

BRIEF SUMMARY OF THE INVENTION

The present invention comprises a series of specific mAbs (6B8, 1B12, 5C2, 2D10, 10H12, etc.) that have high affinity to human FMRP and that show no cross-reactivity to FXR1P or FXR2P. The present invention also includes a polyclonal antibody (R477) generated by immunizing a rabbit with a peptide (DDHSRTDNRPRNPREAK) (SEQ. ID NO. 1) corresponding to a carboxyl domain (starting at aa. residue 554) of human FMRP. R477 Ab binds with high specificity and avidity to FMRP.

The present invention further comprises a xMAP® microsphere (LUMINEX®) based, enzyme-linked immunosorbent assay (ELISA) that allows the detection and quantification of FMRP in blood samples and other tissues. First, the Xmap microspheres are coated with any of the above mentioned high avidity mAbs to capture FMRP from the specimen. Next, the microsphere-mAb-FMRP complex is reacted with anti-FMRP R477 Ab. Finally, anti-rabbit IgG Ab conjugated to phycoerythrin is added. The fluorescence emitted from the result of this process is a function of the amount of FMRP present in the specimen and may be detected using the LUMINEX®-200 System.

The assay may be used to detect FMRP in human lymphocytes, platelets, dried blood spots, cultured chorionic villi cells, lymphoblastoid cell lines, mouse or human brain extracts and other tissues. As expected by those of skill in the art, the assay does not detect FMRP in lymphocytes isolated from full mutation (FM) male Fragile X patients, in lymphoblastoid cell lines derived from male FM FX individuals, and in brain extracts from the Fmrl KO mouse. Low levels of FMRP are detected in specimens derived from male FM size mosaic and methylation mosaic patients.

Micropheres are available in 100 distinctly colored sets each exhibiting a unique signature that is recognized by the LUMINEX® System. Using two or three different microsphere sets, where each set is coupled with a different specific anti-FMRP mAb, the present invention provides a multiplex capture sandwich immunoassay for the detection in the same well of FMRP by more than one antibody. The FMRP signal is compared to that of bona-fide lysates from normal individuals (or mice) and is quantified using as standards recombinant fusion proteins carrying only the capture and detection domains of FMRP. The assays may be performed in 96-well-plates and can be completed in 24 hours.

The present invention may be used to detect and quantify FMRP from dried blood spots (DBS). In this method, drops of blood are spotted onto a collection card (Whatman, WB10001.4) and air-dried for a few hours. The matrix in the card lyses cells, denatures proteins and inhibits the growth of microorganisms. While blood samples (6 to 8 ml) must be stored in a refrigerator and processed for isolation of lymphocytes or platelets as soon as possible (hours from acquisition), DBS cards preparation requires collection of small blood samples (about 20 μl per spot) that are drawn by lancet from the finger, heel, or toe of a neonate. The cards can be stored at room temperature in low gas-permeability plastic bags and sent by regular mail to a laboratory for testing. DBS are used routinely for neonates screening of metabolic diseases, serum protein levels, intracellular enzymes, viruses, and genetic disorders. Moreover, measurement of FMRP in DBS can be performed along with other metabolic markers in a multiplex capture LUMINEX® immunoassay for simultaneous measurement of a wide range of proteins found in blood such as the conventional inflammatory markers or neurotrophins, regularly performed on neonatal dried blood spots by immunoassay with the xMap technology. Our assay can easily be incorporated into a routine protein marker screening of neonatal DBS.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 6:
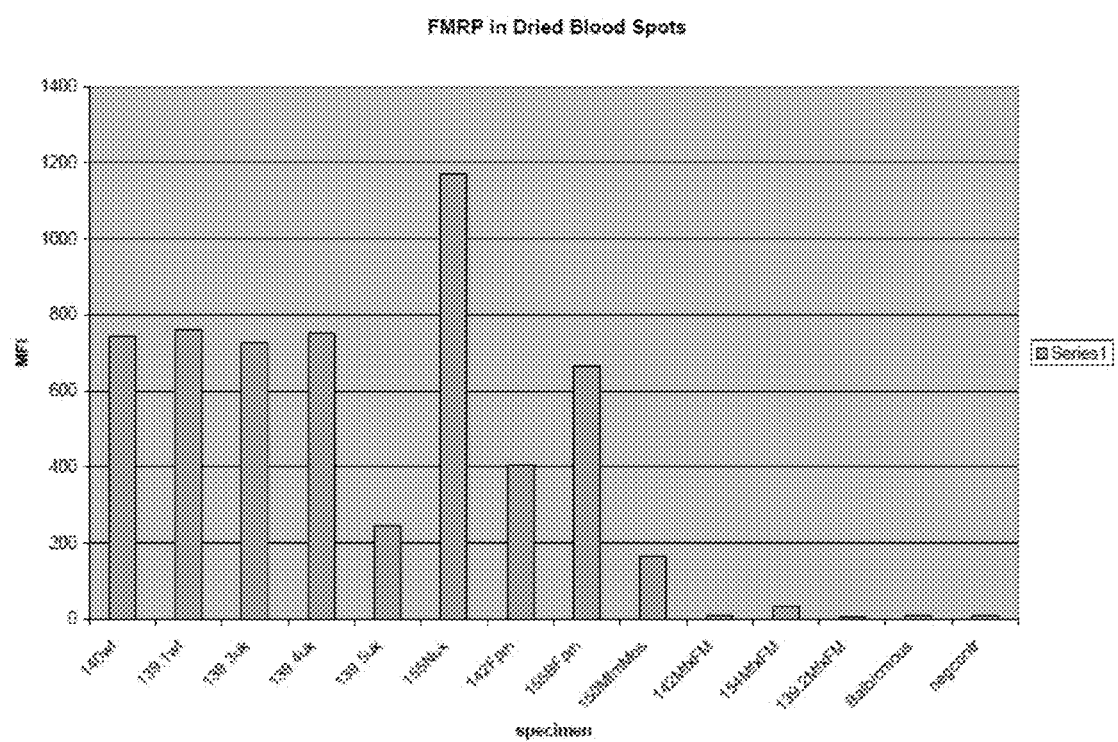
Figure 7A:
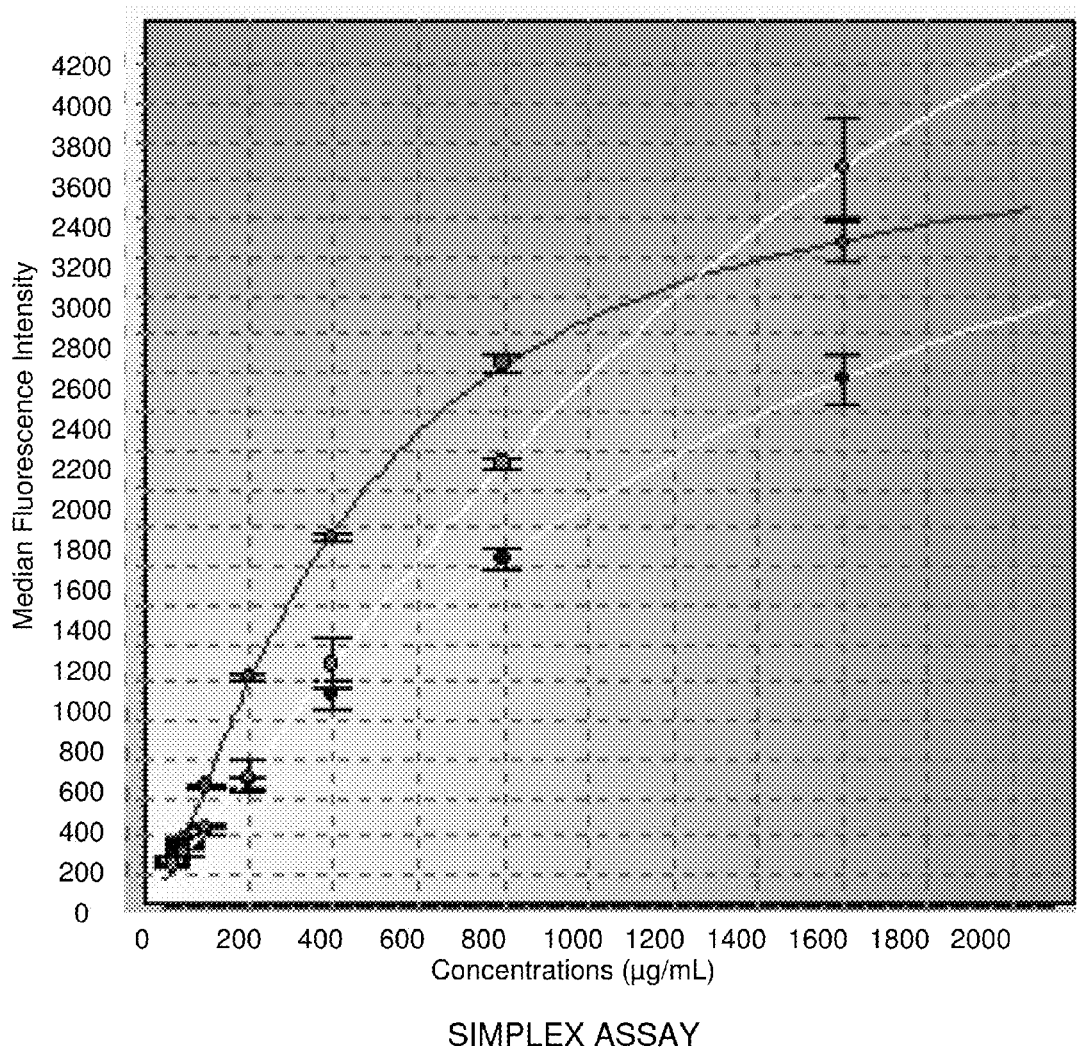
Figure 7B:
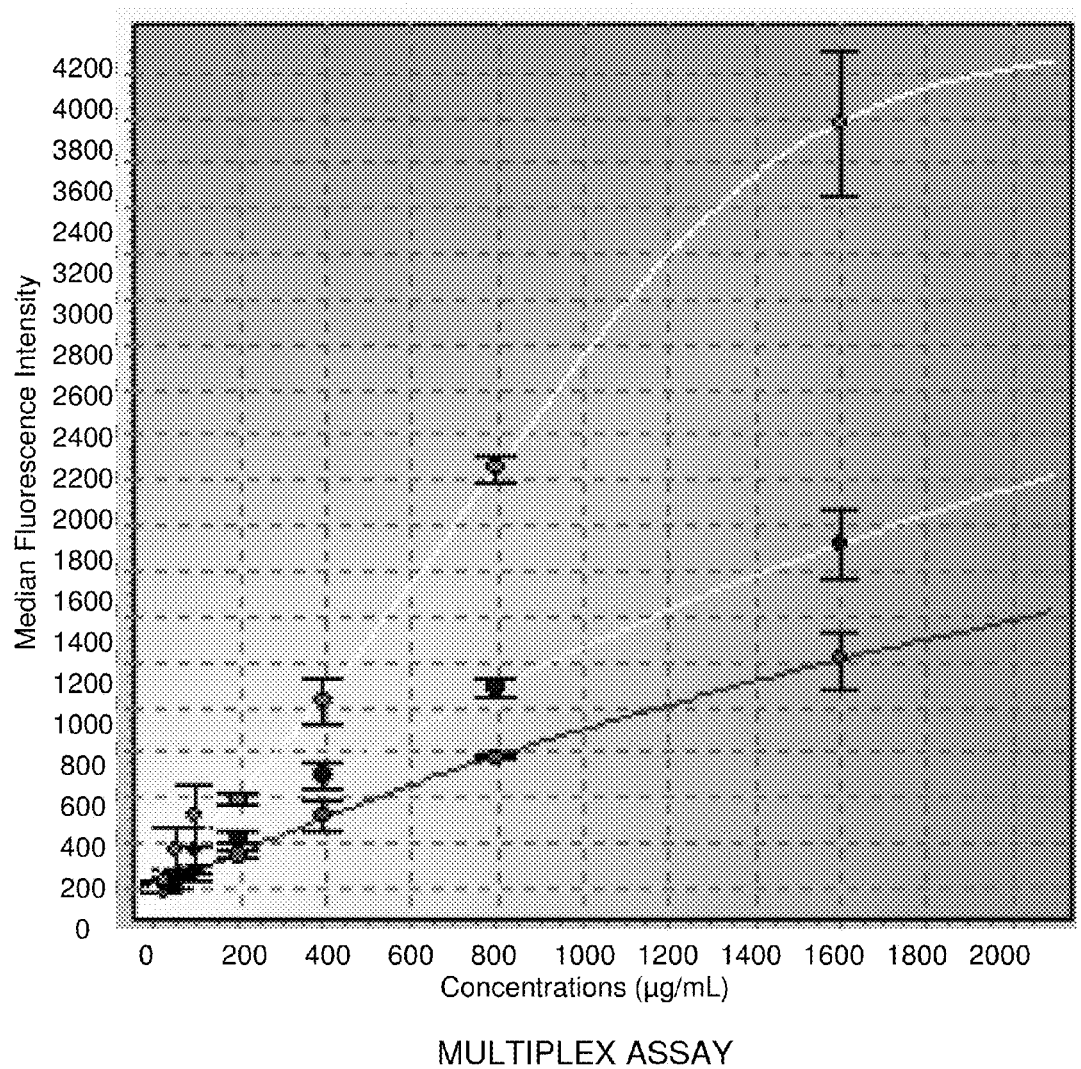

FIG. 6 is a histogram of FMRP detection in DBS where the MSI values were produced from DBS from normal, premutation and FX individuals and capture was done using mAb 6B8 coupled microspheres. More specifically, specimens 140wt, 139.1wt are from normal male individuals and were used as positive controls; Balb/cJ mouse brain homogenate was used as negative control since mouse FMRP does not bind to mAb 6B8; negative control was done without FMRP; specimens 142MfxFM, 154MfxFM, 139.2MfxFm are from male full mutation FX individuals; specimen 150MfmMos is from a male mosaic full mutation individual; specimens 124Fpm and 155BFpm are from female premutation individuals; and the other specimens are from individuals whose FX status had not been determined;

FIGS. 7A and 7B are graphs of median fluorescence intensity verses concentration of total protein from lymphocytes of a normal individual where both experiments were done using three sets of xMAP® microspheres each coupled to one mAb, i.e., 5C2, 6B8, and 2D10. FIG. 7A depicts an experiment performed using capture mAb in a separate well (simplex) and FIG. 7B depicts an experiment performed using all three mAbs in the same well (multiplex).

Figure 8:
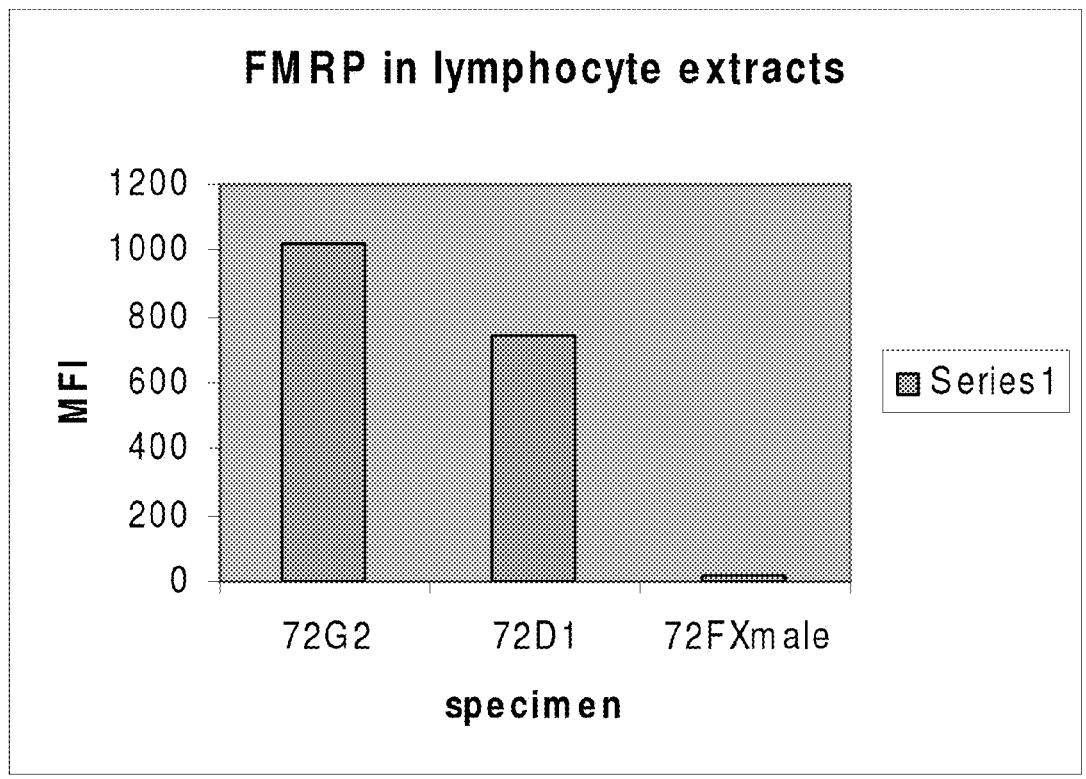
Figure 9:
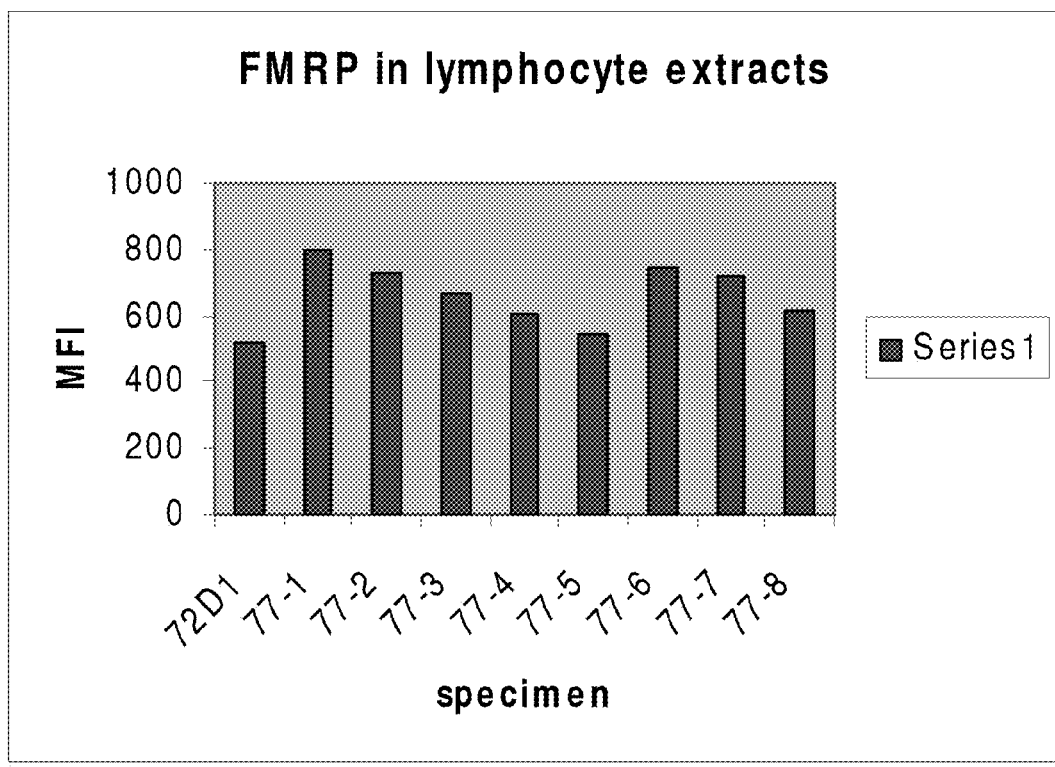
Figure 10:
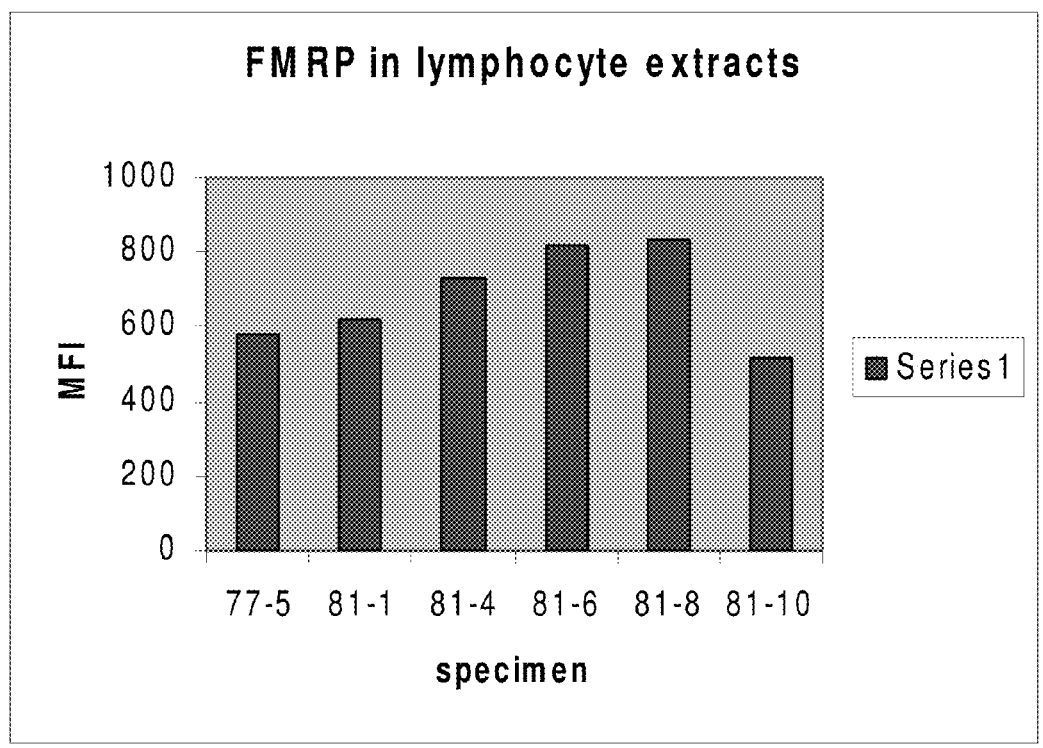
Figure 11:
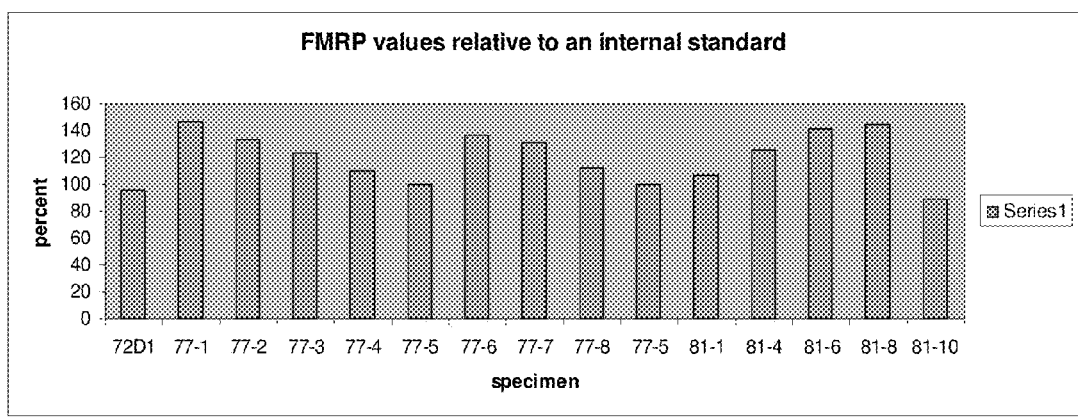
Figure 12:
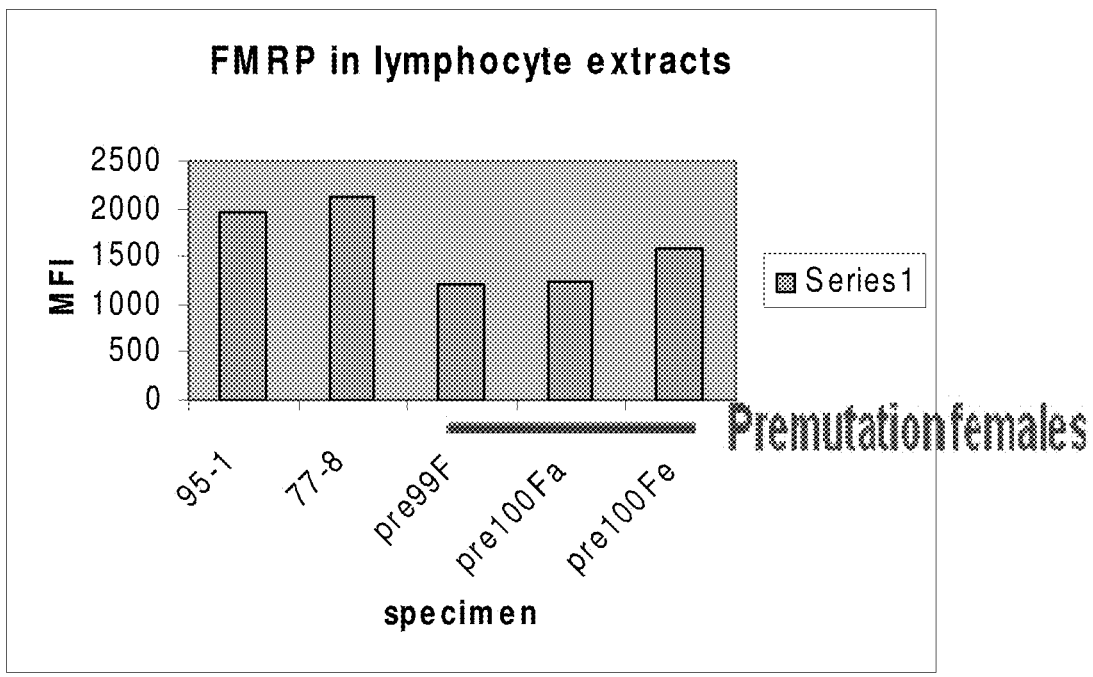
Figure 13:
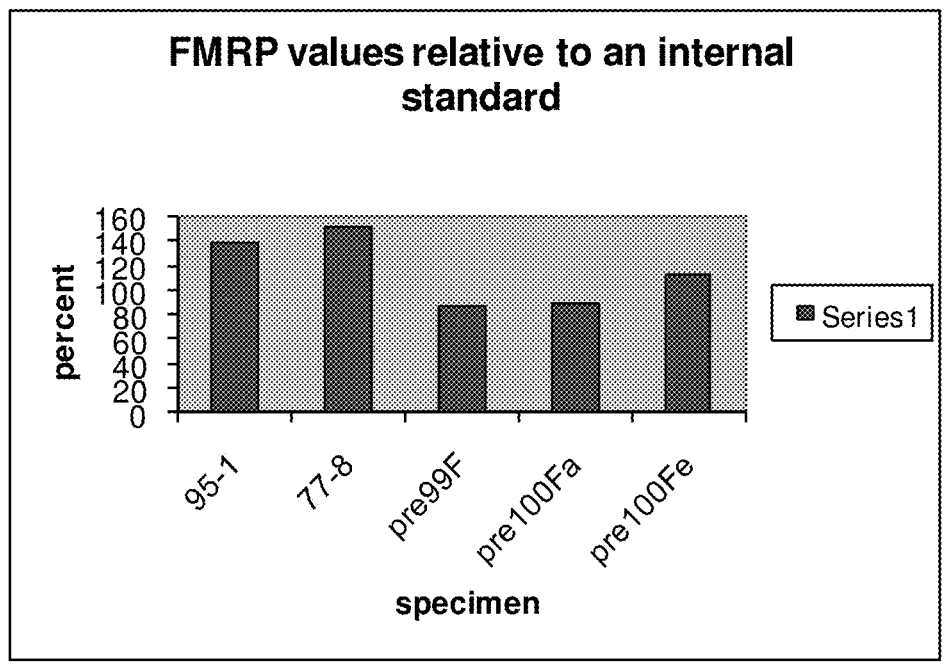

FIG. 8 is a chart of median fluorescence intensity for the detection of FMRP using mAb 6B8 coupled xMAP® microspheres to capture where specimens 72G2 and 72D1 are from normal individuals and 72Fxmale is from a male FM Fx patient., and capture was done using mAb 6B8;

FIG. 9 is a chart of median fluorescence intensity showing the detection of FMRP in lymphocyte extracts from nine normal individuals where capture was done using mAb 6B8;

FIG. 10 is a chart of median fluorescence intensity showing the detection of FMRP in lymphocyte extracts f from six normal individuals where capture was done using mAb 6B8;

FIG. 11 is a chart of FMRP values relative to an internal standard for several specimens using mAb 6B8;

FIG. 12 is a chart of fluorescence detection of FMRP in lymphocyte extracts from normal individuals (95-1 and 77-8) and from three permutation women (pre99F, pre100Fa and pre100Fe where capture was done with mircospheres coupled to mAb 6B8;

FIG. 13 is a chart of FMRP values relative to an internal standard (a bona-fide lymphocyte extract) for specimens described in FIG. 12.

FIG. 14A-C is a series of Western blots showing the capture assay pair with lymphocyte extracts from a FXS patient using (A) mAb68B, (B) R477, and (C) mAb1C3 with overexposed films in the middle section and sample loading shown in the bottom section with an anti-GAPDH antibody.

Figure 15:
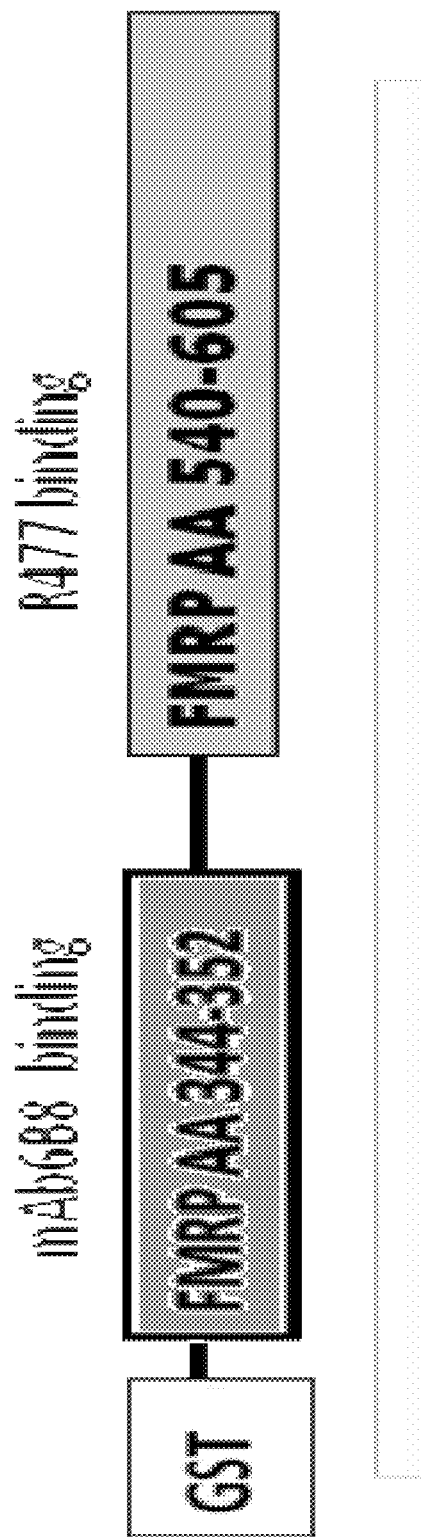
Figure 16:
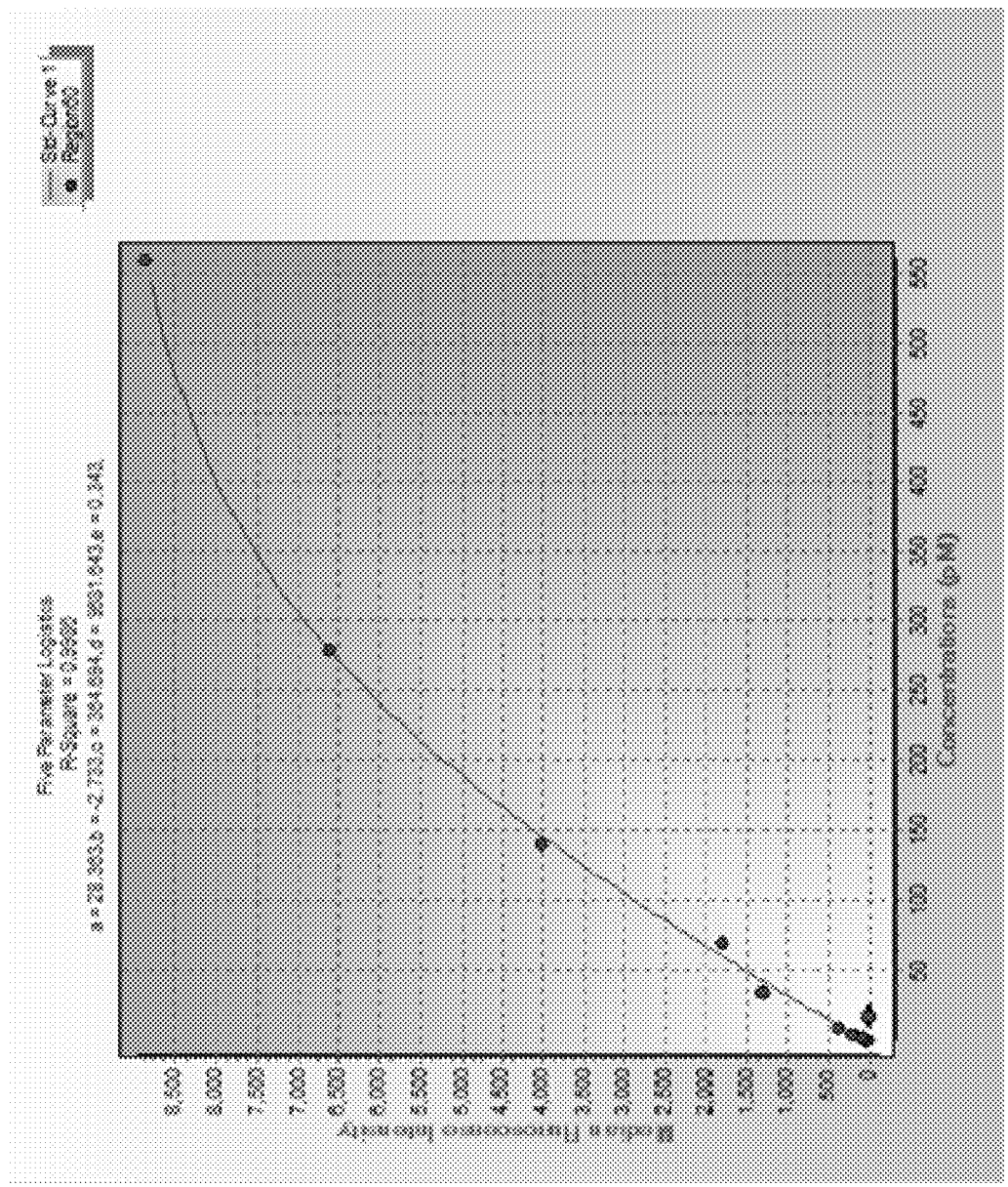
Figure 17:
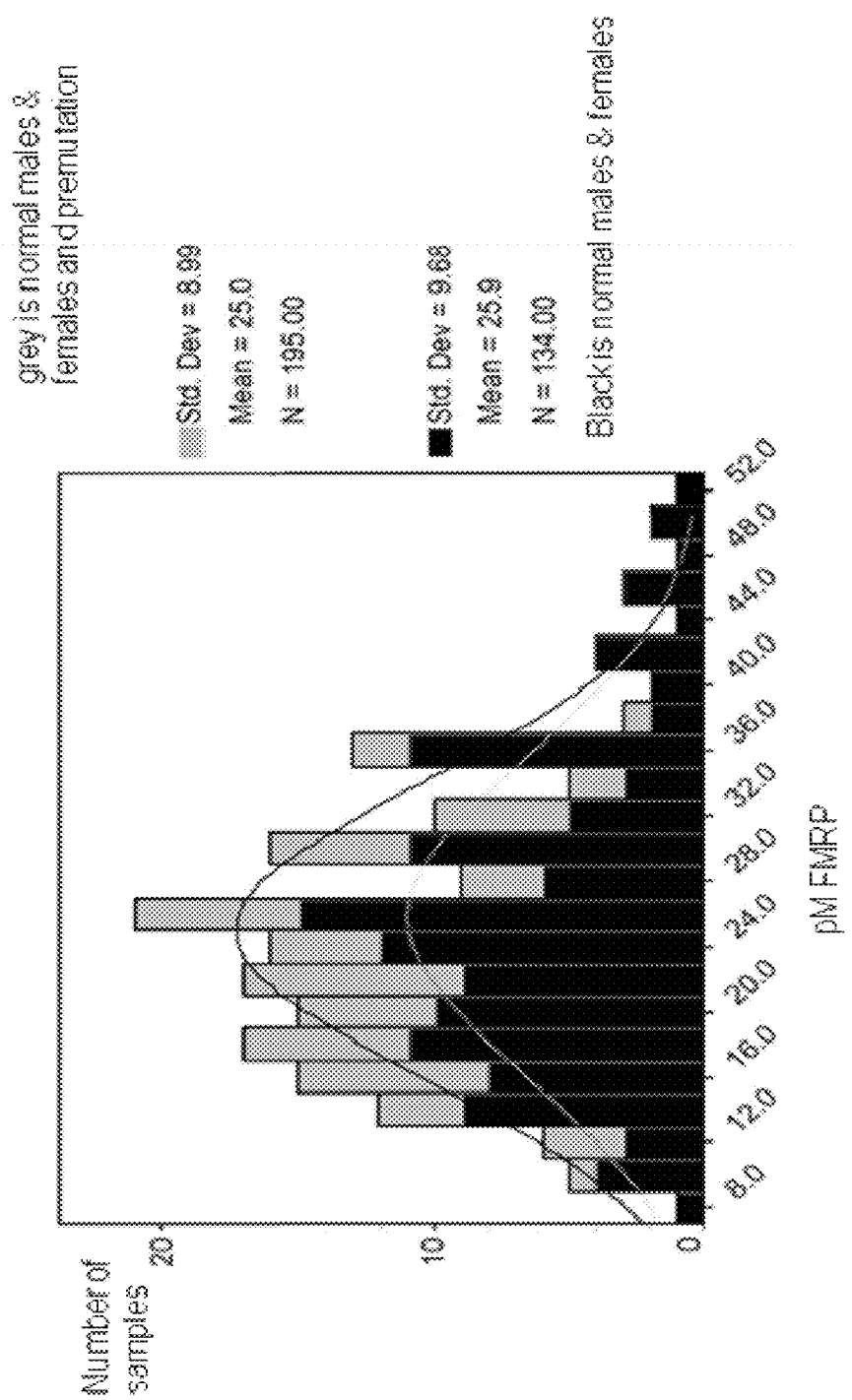
Figure 18:
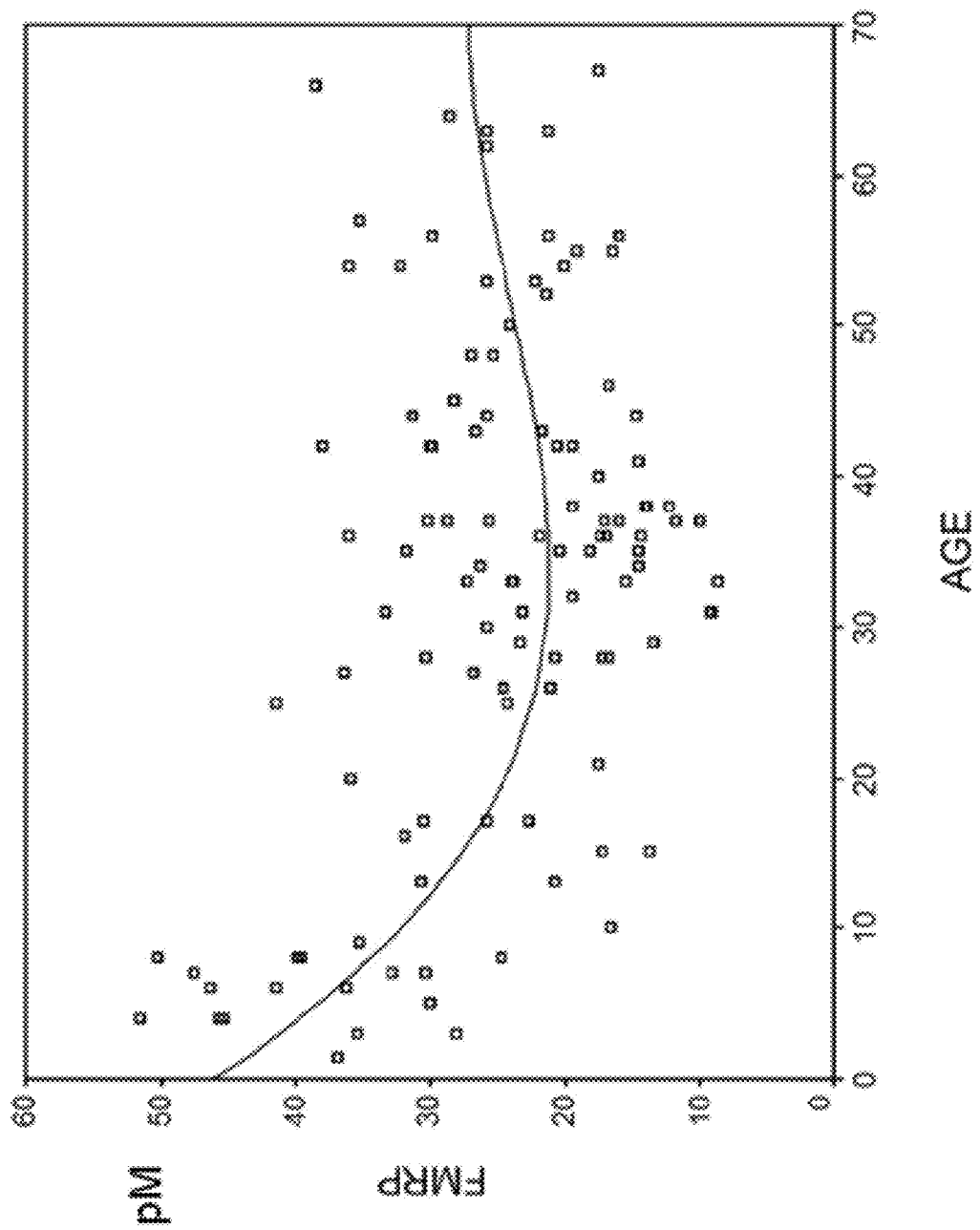
Figure 19:
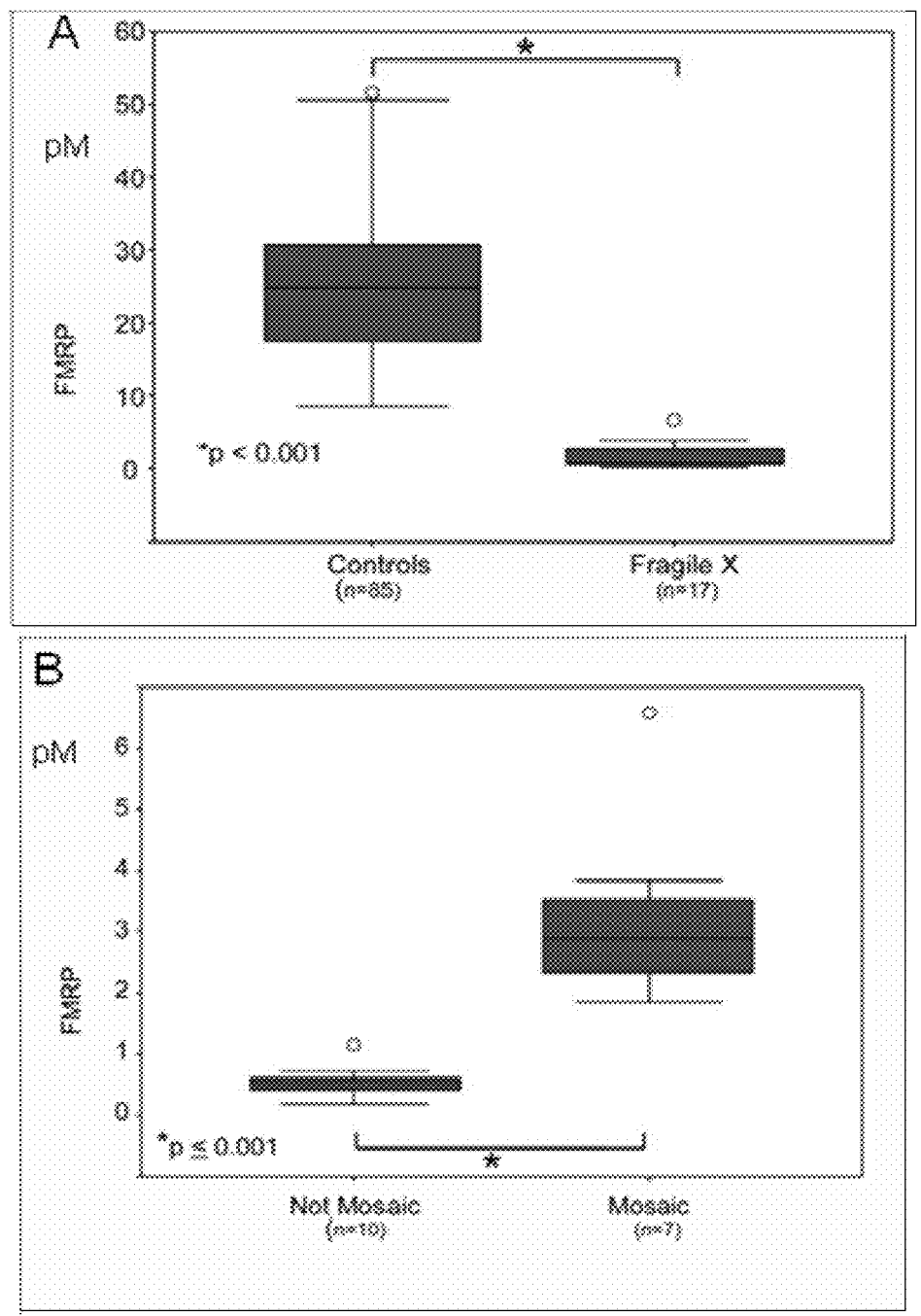
Figure 20:
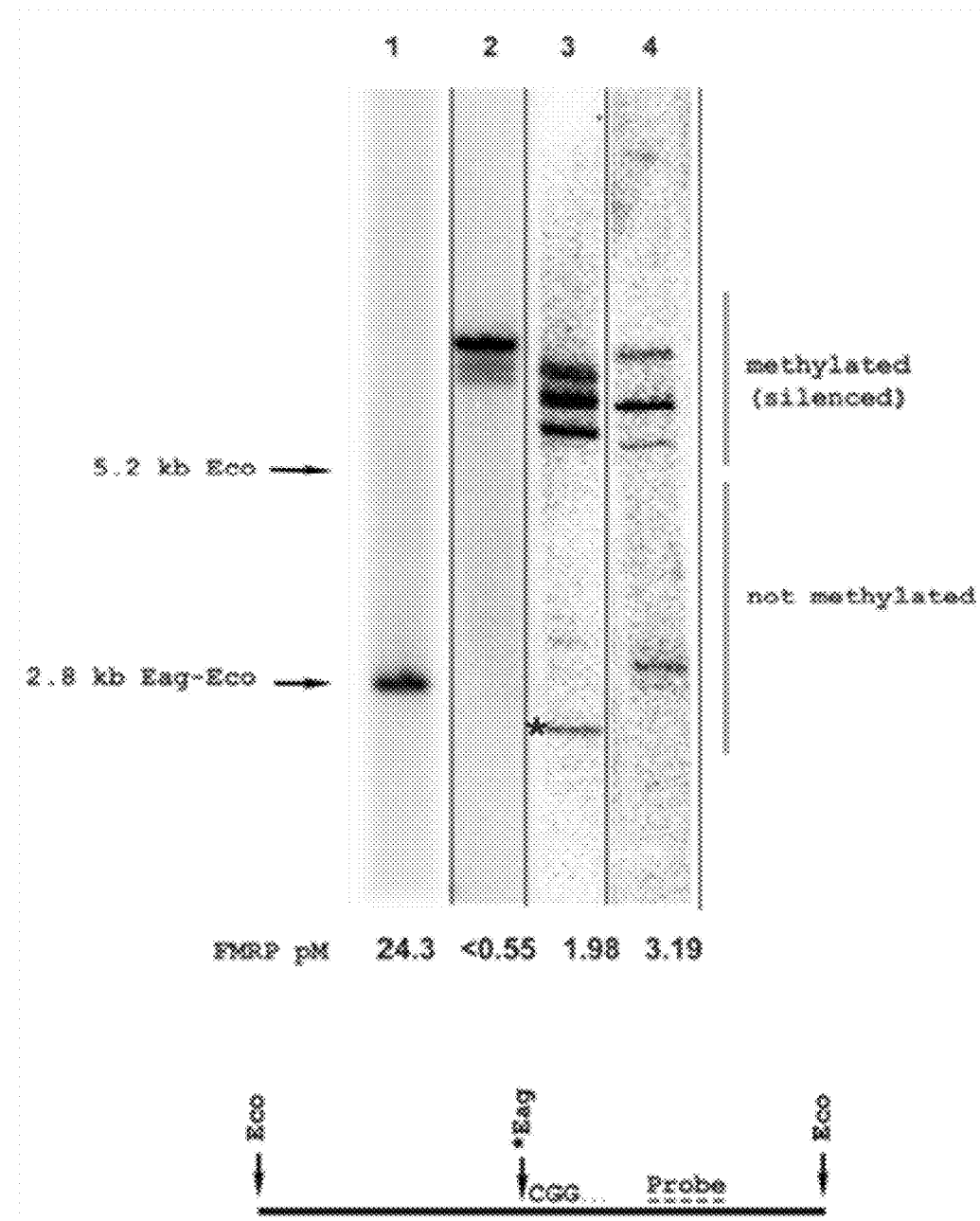

FIG. 15 is a schematic of the mAb6B8 and R477 epitope domains;

FIG. 16 is a graph of the dose response curve of fluorescence (MFI) as a function of GST-SR7 concentration;

FIG. 17 is a series of graphs of the levels of FMRP in DBS with variable expression of FMRP in normal individuals (black, N=134) and in normal plus permutation individuals (grey, N=195);

FIG. 18 is plot of FMRP levels in normal individuals as a function of age;

FIG. 19 is a series of charts comparing FMRP expression in males, where (A) is full mutation (N=17) and normal (N=85), and (B) is mosaic (N=7) and non-mosaic (N=10) full mutation groups;

FIG. 20 is a Southern blot analysis of genomic DNA isolated from a normal male (lane 1), a FM male (lane 2) and two mosaic FM males (lanes 3 and 4);

FIG. 21 is a chart of a comparison of FMRP level in females with full mutation alleles to females with normal or permutation alleles (N=88) using the Mann-Whitney test, where (A) is a plot analysis showing significantly lower levels of FMRP in full mutation (p=0.03) and (B) is a Receiver-Operating Characteristic (ROC) curve showing that at a cutoff of 13.7 pM, the assay for full mutation females gives a sensitivity of 20% and a specificity of 93%.

DETAILED DESCRIPTION OF THE INVENTION

Figure 1:
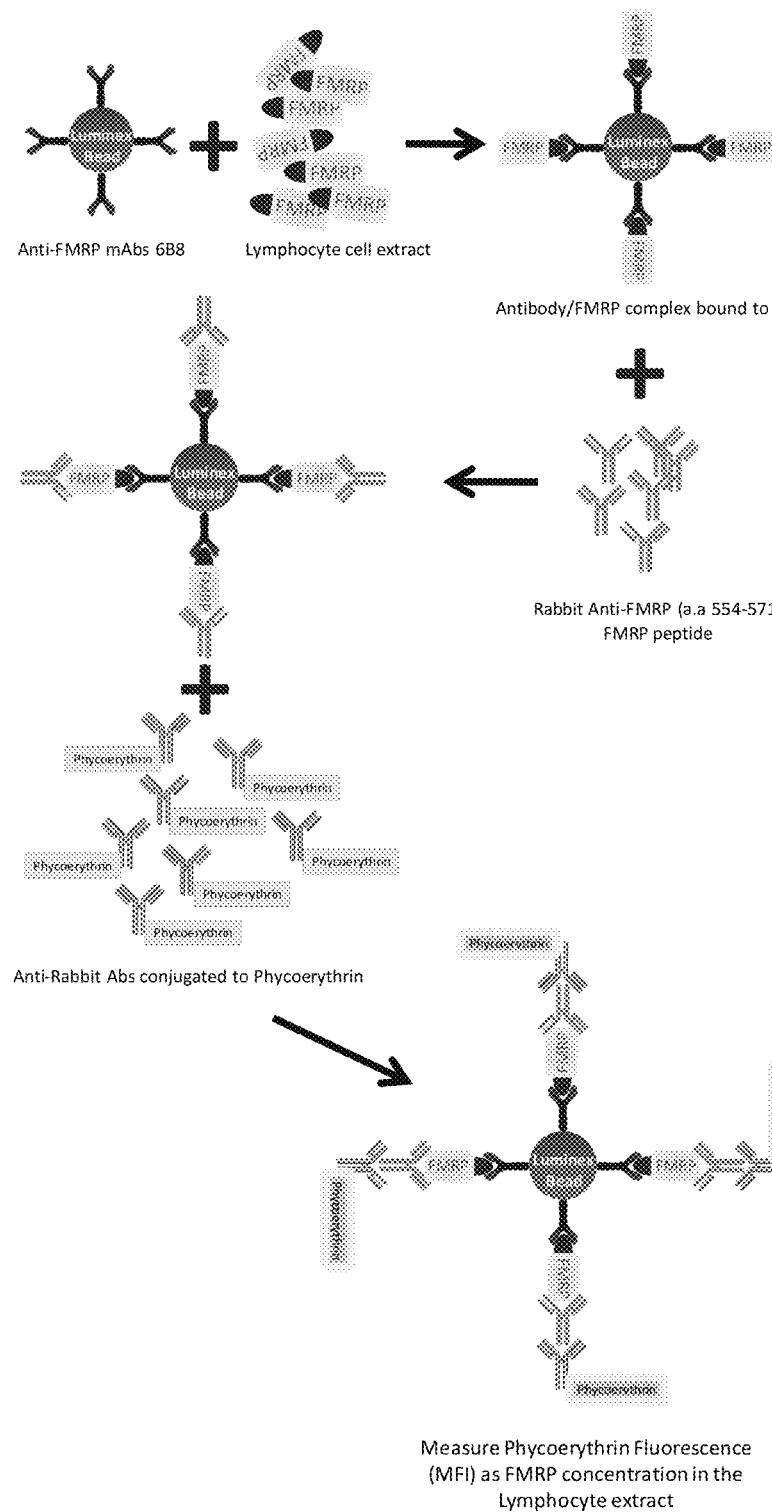
FIG. 1 is a schematic of the system and method for the detection of FMRP in a tissue sample according to the present invention.
Figure 2:
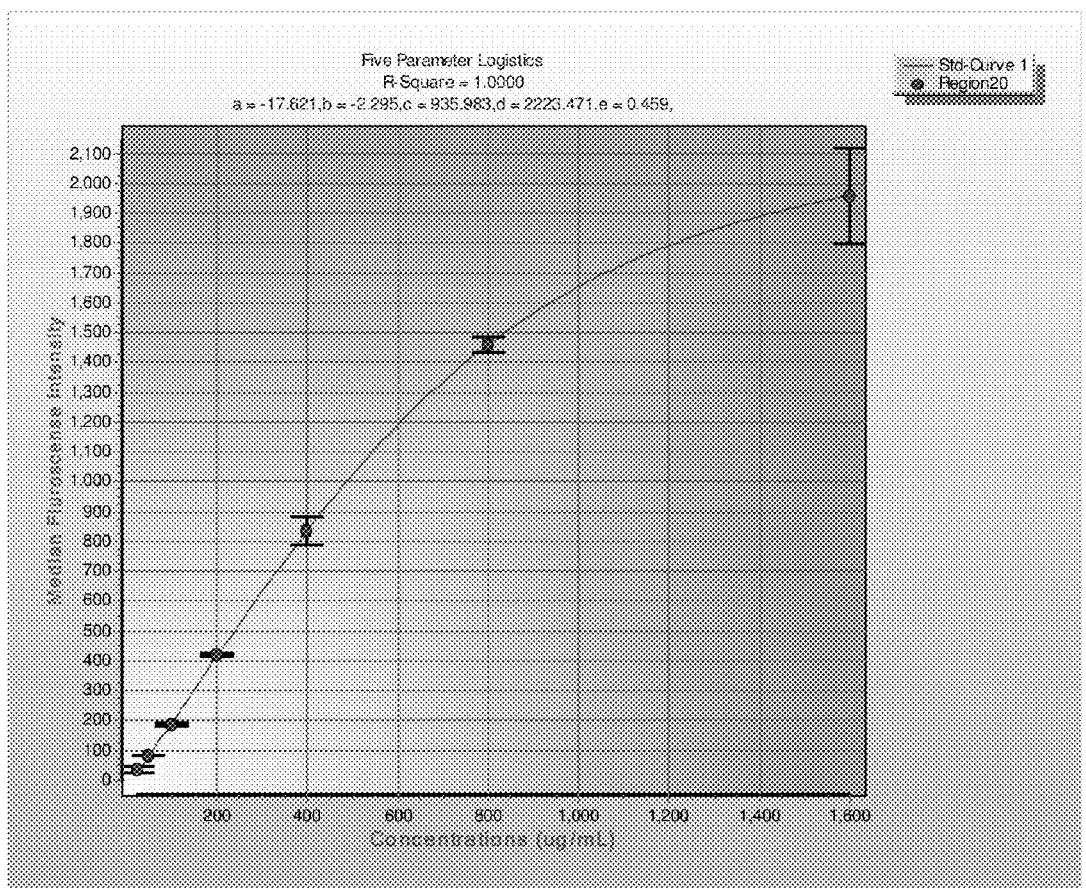
FIG. 2 is a graph of the median fluorescence intensity verses the concentration of total protein for mAb 5C2 using mouse brain tissue samples.
Figure 3:
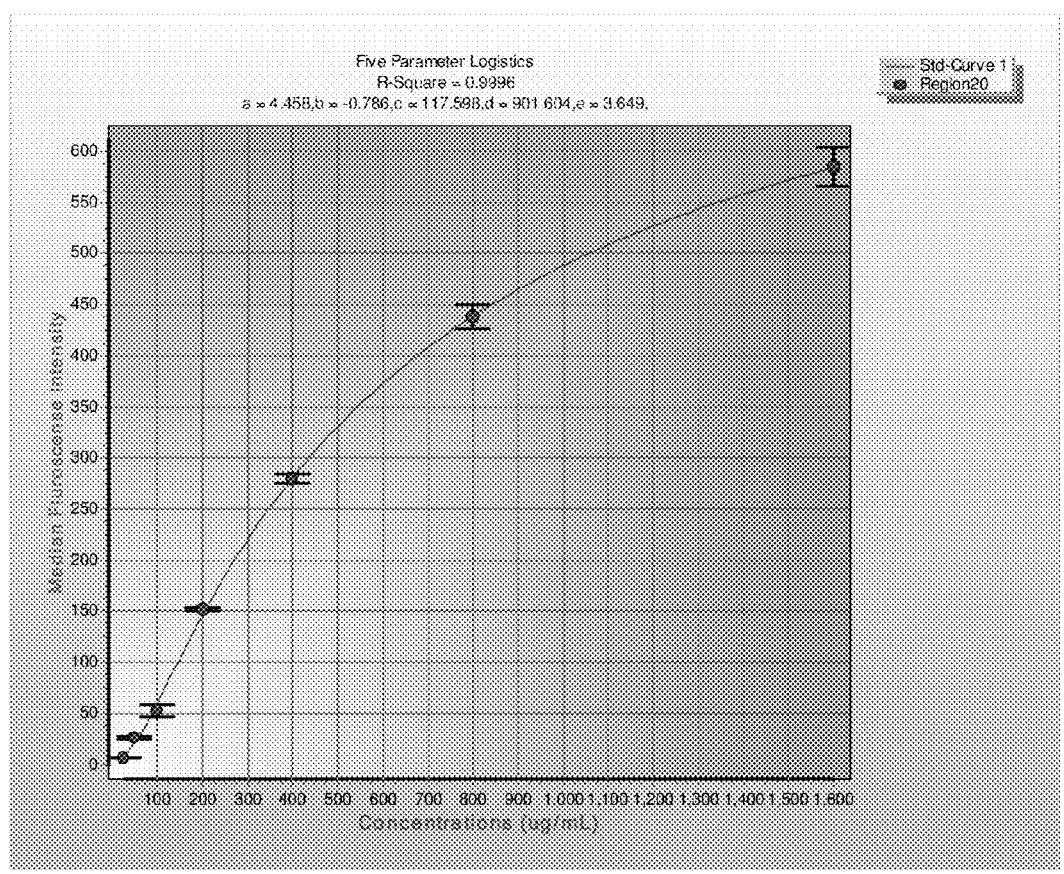
FIG. 3 is a graph of the median fluorescence intensity verses concentration of total protein for mAb 5C2 using a human lymphoblastoid cell line derived from a normal individual.

Referring to the Figures, wherein like numerals refer to like parts throughout, there is seen in FIG. 1 a pathway for the detection and measurement of FRMP according to the present invention. More particularly, anti-FMRP mAbs (preferably bound to Xmap microsphere beads) are mixed with a target tissue sample extract containing FMRP to form an antibody FMRP complex bound to the beads. Rabbit anti-FMRP antibody is then attached to the complex. An anti-rabbit IgG Ab conjugated to phycoerthrin is then added so that the amount of phycoerthrin fluorescence may be measured to determine the quantity of FMRP bound to the beads.

As described above, the present invention includes a number of new anti-FMRP monoclonal antibodies that exhibit a high affinity for the capture of human FMRP without exhibiting cross-reactivity to related proteins FXRP1 or FXRP2. The mAbs according to the present invention were produced in the IBR Monoclonal Antibodies Facility using recombinant mouse FMRP and human FMRP. These proteins were expressed in Sf9 insect cells infected with baculovirus engineered to carry either the mouse or the human FMR1 gene. The recombinant proteins were expressed, purified in large scale, and used for immunizing mice and for hybridoma screening. Several rabbits were immunized with a FMRP peptide (17-aa long position 554 to 570), i.e., (DDHSRTDNRPRNPREAK) (SEQ. ID NO. 1). A rabbit anti-FMRP R477 polyclonal antibody produces a particularly strong response with high affinity and avidity to the protein. The purified R477 Ab reacts strongly to the immunogen peptide and FMRP from a variety of sources: including mouse brain extracts, human lymphocyte extracts, platelets, lymphoblastoid cell lines, lymphocyte extracts and dried blood spots. This antibody serves as the detection reagent in the protein-based LUMINEX® assay.

The epitopes of mAbs 1B12 and 6B8 have been determined (see Table 1 below). The other mAbs have been found to bind to a domain of FMRP (Table 1).

TABLE 1

| mAb | FMRP Domain (aa) | Epitope |
|-----|------------------|---------|
| 1F1 | 442-540 | NA |
| 1E3 | 320-354 | NA |
| 1B12 | 329-375 | GPNA/SP/SEE (SEQ. ID NO. 2) |
| 2G5 | 76-132 | NA |
| 3E7 | 442-540 | NA |
| 5C2 | 320-375 | NA |
| 2D10 | 396-431 | NA |
| 3H8 | 320-375 | NA |
| 10H12 | 442-540 | NA |
| 6B8 | 320-375 | SRVGPN (SEQ. ID NO. 3) |
| 7F9 | 442-540 | NA |

Table 2 below illustrates the phycoerythrin fluorescence measured as a function of the total amount of protein for two of the antibodies 5C2 and 2D10 of the present invention, and with an anti-PrP mAb, 3F4. The latter mAb, as expected by people of skill in the art, did not react with FMRP and was used as negative control.

TABLE 2

| Antigen μg | Mouse Brain | | | H Lymphobl control | | | H Lymphobl FX male | | |
|---|---|---|---|---|---|---|---|---|---|
| | Capture Beads = 5C2 | | | | | | | | |
| 80 | 1879 | 2106 | 14 | 629 | 601 | 13.5 | 27 | 18.5 | 16 |
| 40 | 1475 | 1514 | 16 | 477 | 460 | 17 | 20.5 | 20 | 16 |
| 20 | 835 | 899 | 18 | 313 | 307 | 18 | 20 | 19 | 16 |
| 10 | 459 | 449 | 18 | 184 | 181 | 17 | 22 | 22 | 21 |
| 5 | 226 | 216 | 22 | 80 | 88 | 18 | 24 | 23 | 22.5 |
| 2.5 | 116 | 113 | 22 | 56 | 58.5 | 22 | 25 | 23.5 | 23.5 |
| 1.25 | 74 | 61 | 12 | 38 | 37.5 | 22 | 22 | 26 | 22 |
| 0 | 34 | 32 | 31 | 28 | 33 | 26 | 27 | 24 | 26 |
| | Capture Beads = 3F4, anti PrP | | | | | | | | |
| 80 | 51 | 49 | 4 | 6 | 6 | 3 | 5 | 4 | 3 |
| 40 | 36 | 39.5 | 4 | 5 | 6 | 4 | 4 | 4 | 4 |
| 20 | 17.5 | 18 | 4 | 5 | 6 | 4 | 4 | 5 | 4 |
| 10 | 11 | 10 | 4 | 5 | 4 | 4 | 5 | 5 | 4 |
| 5 | 7 | 8 | 3 | 5 | 5 | 3 | 5 | 6 | 4 |
| 2.5 | 7 | 6 | 0 | 6 | 6 | 4 | 5 | 5 | 5 |
| 1.25 | 7 | 5 | 0 | 5 | 5 | 5 | 5 | 4.5 | 4 |
| 0 | 6 | 6 | 4 | 6 | 6 | 5 | 6 | 5 | 4 |
| | Capture Beads = 2D10 | | | | | | | | |
| 80 | 447 | 528 | 26 | 275 | 317 | 28 | 35 | 32 | 28 |
| 40 | 289 | 309 | 28 | 181 | 182 | 28 | 35 | 34 | 32 |
| 20 | 138 | 139 | 31 | 94.5 | 111 | 32 | 33 | 32.5 | 28 |
| 10 | 72 | 68 | 31 | 64 | 66 | 32 | 35 | 34 | 30 |
| 5 | 47 | 47 | 29.5 | 47.5 | 45 | 32.5 | 33 | 31.5 | 29 |
| 2.5 | 40 | 41 | 25.5 | 41 | 41 | 34 | 31 | 30.5 | 28 |
| 1.25 | 41 | 27 | 0 | 36 | 35 | 32 | 29 | 31 | 28 |
| 0 | 38 | 39 | 39 | 35 | 38 | 31 | 34 | 31 | 30 |

As seen in the above Table 2 and in FIGS. 2-8, mAb 2D10 reacts to both human and mouse FMRP. mAb 6B8 reacts strongly to human, but not mouse FMRP. Both of these antibodies were derived from mice immunized with human recombinant FMRP. Additional antibodies (see Table 1) include mAb 5C2 and 1B12 derived from mice immunized with mouse recombinant FMRP are reactive to both mouse and human FMRP.

Figure 4:
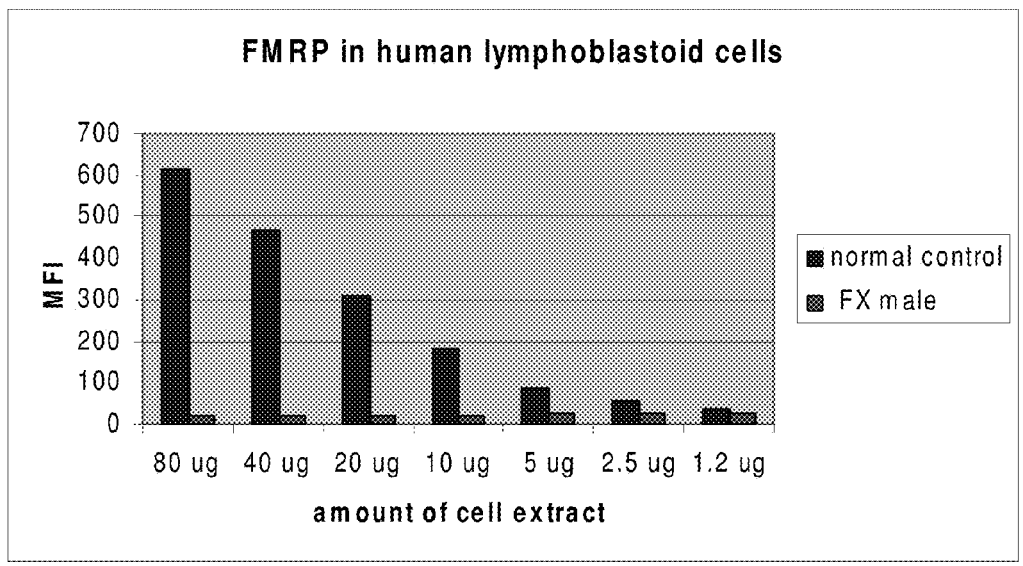
FIG. 4 is a chart of median fluorescence intensity verses total amount of protein extract from human lymphoblastoid cells (normal control and FM FX male patient) using mAb 5C2.
Figure 5:
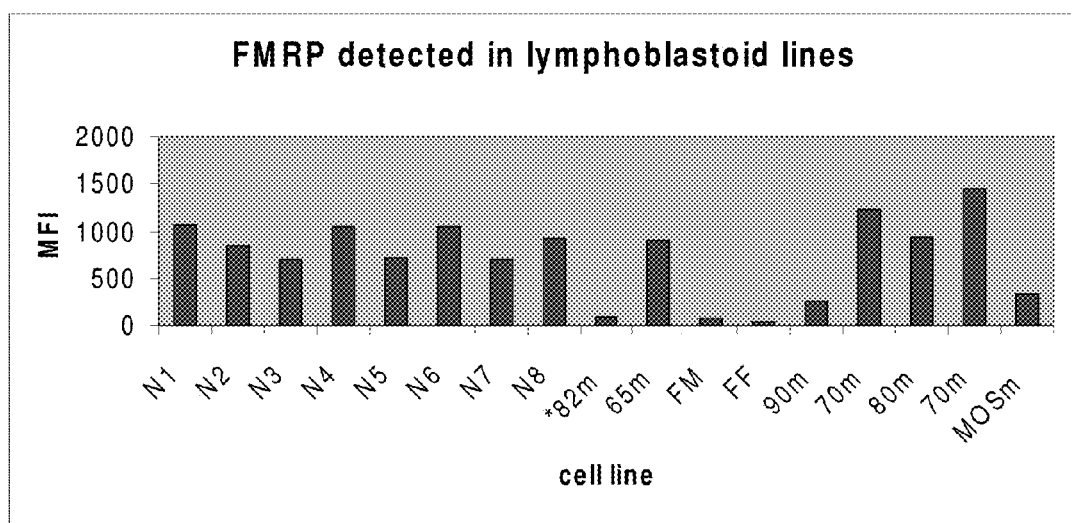
FIG. 5 is a chart of median fluorescence intensity detection of FMRP in several control (N1-N8) and target lymphoblastoid cell lines using mAb 5C2.

There is seen in FIGS. 4 and 5 an assay displaying the MFI verses total protein amount of lymphoblastoid cells extract from a normal individual and from a FM FX patient. Whereas the MFI obtained from the normal specimen was dependent on the amount of total protein, the MFI obtained with the FX specimen did not show any variation.

There is in FIG. 6 an assay done using Dried Blood Spots and mAb 6B8 xMAP® microspheres. Specimens from normal male individuals were used as positive controls and produced MFI values around 750. A mouse specimen was used as negative control since the capturing 6B8 microspheres do not bind to mouse FMRP. Specimens from full mutation FX males produced MFI values of 10 to 30. A specimen from a mosaic FM FX patient showed a MFI of 150. Premutation samples showed either normal MFI values or slight lower MFI. The results cleary indicate to those that know the art that the DBS assay can be used to screen for male FM FX and male mosaic FM individuals.

There is shown in FIGS. 7A and 7B assays performed with three diverse xMAP® microspheres coupled either with mAb 5C2, 6B8, or 2D10. Two experiments were performed using a normal lymphoblastoid cell line extract. In one experiment, each set of coupled microspheres were placed in separate wells (Simplex assay), in the other all three sets were used in the same wells (Multiplex assay). In both experiments, microspheres coupled with mAb 6B8 produced higher MFI than the other two sets. The Multiplex experiments shows that when used in the same well 6B8 microspheres still maintain high MFI while the other two sets produce lower MFI with respect to those obtained in the Simplex assay. To those of skill in the art, the data indicate that mAb 6B8 has higher affinity to human FMRP than the other two mAbs. Table 3 below describes the specimens used in FIG. 5.

TABLE 3

| Sample | Genotype | Sex | CGG | MFI | Cell line |
|---|---|---|---|---|---|
| N1 | Control | male | normal | 1060 | GM4736 |
| N2 | Control | female | normal | 851 | GM7000 |
| N3 | Control | NA | normal | 691 | GM7113 |
| N4 | Control | male | normal | 1041 | GM6994 |
| N5 | Control | female | normal | 723 | GM7010 |
| N6 | Control | female | normal | 1047 | GM7036 |
| N7 | Control | male | normal | 691 | GM7352 |
| N8 | Control | female | normal | 919 | GM7436 |
| 82m | mosaic | male | 82, >200 | 97 | C4079 |
| 65m | premutation | male | 65 | 901 | C6711 |
| FM | full mut | male | >200 | 80 | C2159 |
| FF | full mut | female | 30, >200 | 35 | C8027 |
| 90m | premutation | male | 90 | 249 | C3907 |
| 70m | Permutation | male | 70 | 1236 | C5557 |
| 80m | Permutation | male | 80 | 932 | C2274 |
| 70m | Permutation | male | 70 | 1450 | C3137 |
| MOSm | mosaic mut | male | >200 | 331 | C10148 |

There is seen in FIG. 8, an assay displaying the median fluorescence intensity (MFI) (the median Fluorescene value detected by the system after reading 100 microspheres) for two normal control and one Fragile X male lymphocyte extract. Note the nearly zero MFI for the Fragile X lymphocyte extract compared to the 100 fold higher values for the two control lymphocyte extracts. This 100 fold difference is highly reproducible relative to male full mutation FX individuals.

There is seen in FIGS. 8-10 the detection of FMRP in lymphocytes derived from the normal population (14 samples) where MFIs varied from 550 to 800. FIG. 11 depicts these values are compared to the internal lymphocyte standard 77-5. Despite the use of identical protein concentrations for these assays, there is a wide variation in the MFI levels. The cause of these variations are not known.

There is seen in FIGS. 12 and 13 the MFIs for lymphocyte extracts from two controls and three premutation females. Note the intermediate MFIs for the lymphocyte extracts from the premutation females compared to the extracts from the control subjects. These figures reflect the MFIs relative to the internal lymhocyte standard. While the MFIs for all three premutation females were lower than the two control MFIs, the variation in control MFI values does not allow a statistical comparison.

EXAMPLE 1

The method for detecting and measuring FMRP according to the present invention may be used in connection with human lymphocytes as follows. First, mononuclear cells are isolated from blood using BD Vacutainer CPT (Becton Drive, Franklin Lakes, REF 362760) according to the BD protocol. Cells are lysed in M-Per (Invitrogen) buffer supplemented with 150 mM NaCl, chymostatin (10 µg/ml), antipain (10 µg/ml, and 1/200 dilution of Protease inhibitor cocktail set III (Calbiochem), and sonicated using a Branson Digital Sonifier 250 (Denbury, Conn.). Cell debris are removed by centrifugation at 16,000×g at 4° C. for 15 min and the protein concentration is determined (Micro BCA Assay kit; Thermo Scientific, Rockford, Ill.). Samples are diluted in assay buffer (PBS, 1% BSA, 0.05% Tween 20, 0.05% Na Azide).

LUMINEX®-based ELISA protocols are well known to those of skill in the art, and will not be described here in detail. In brief, microspheres (about 5,000) that are coupled with the chosen anti-FMRP mAb are mixed in a well of a Multiscreen Filter Plate (MSBVN1210—Millipore, Billerica, Mass.) with the lysates (100 µl total volume) and incubated on a plate shaker at room temperature in the dark for 4 hours. A serial dilution of a lymphocyte extract (in duplicate wells, starting at 5 µg total protein per well) from a normal individual and/or a recombinant fusion protein are/is used as standards to quantify FMRP. The supernatant is aspirated using a vacuum manifold, the microspheres are washed 3 times, re-suspended in 100 µl of assay buffer containing 2 µg/ml of R477 Ab, and incubated on a plate shaker overnight. The liquid is aspirated, the microspheres washed and incubated with 100 µl of anti-rabbit IgG conjugated to phycoerythrin (2 µg/ml in assay buffer; Invitrogen P2771MP) for 2 hours. After aspirating the liquid, microspheres are re-suspended in 100 µl of assay buffer and analyzed on the LUMINEX® 200.

EXAMPLE 2

The present invention may also be used in connection with lymphoblastoid cell lines as follows. First, pellets of cultured cells (1×107) are homogenized in a dounce homogenizer (20 strokes with the loose pestle) in 1 ml of ice cold buffer (10 mM HEPES H 7.4; 200 rnM NaCl, 0.5% TritonX-100, 30 rnM EDTA, Protease inhibitor) available from Roche. Lysates are transferred into tubes, centrifuged at 6,800×g at 4° C. Supernatant is transferred into fresh tubes, and protein concentration determined as described above. The LUMINEX® capture ELISA is performed as described in above with respect to human lymphocytes.

EXAMPLE 3

The present invention may additionally be used in connection with dried blood spots (DBS). The preparation and use of DBS is well known to those of skill in the art, and will not be described here in detail. In brief, blood samples are spotted onto ID blood staining cards (Whatman, WB100014) and let dry overnight at room temperature. Cards are then wrapped in aluminum foil and stored in sealed plastic bags at room temperature. Disks (7-mm-diameter) are punched from dried blood spots and transferred into a 2-ml screw-cap tube with wide bottom. M-Per buffer (150 µl) supplemented with 150 mM NaCl, chymostatin (10 µg/ml), antipain (10 µg/ml, and 1/200 dilution of Protease inhibitor cocktail set III (Calbiochem) is added and tubes incubated at room temperature on a Belly Dancer at maximum speed for 3 hours. Tubes are centrifuged for 20 sec and supernatant transferred into a fresh tube. Debris is removed by a brief centrifugation step and supernatant (20 µl to 40 µl) diluted in assay buffer. FMRP is detected using the capture ELISA described above.

EXAMPLE 4

The present invention may further be used in connection with platelets. Isolation procedures of human platelets are well known to those of skill in the art and will not be described in detail herein. In brief, blood samples (8 ml) are collected in a vacutainer BD tube (yellow cap, 39 mM citric acid, 75 mM sodium citrate, 135 mM glucose, pH 7.4), and centrifuged at low speed (190×g) for 15 min at room temperature. Platelet-rich plasma is transferred to fresh tubes and centrifuged at 2500×g for 5 min at room temperature. The platelet pellets are lysed in M-Per (Invitrogen) buffer supplemented with 150 mM NaCl, chymostatin (10 µg/m1), antipain (10 µg/ml, and 1/200 dilution of Protease inhibitor cocktail set III (Calbiochem), and sonicated using a Branson Digital Sonifier 250. Debris is removed by centrifugation at 16,000×g at 4° C. for 15 min and protein concentration determined as described above. The LUMINEX® capture ELISA is performed as described above.

EXAMPLE 5

The present assay may be used in connection with mouse brain extracts. Brains are washed in cold PBS and homogenized using in a dounce homogenizer (10 strokes with the loose pestle) in 2 ml/brain of ice cold buffer (10 mM HEPES pH 7.4; 200 mM NaCl, 0.5% TritonX-100, 30 mM EDTA, protease inhibitor (Roche, complete). Debris is removed by centrifugation at 6,800×g at 4° C. Supernatants are transferred to fresh tubes and NaCl is added to a final concentration of 400 mM. Supernatants are clarified by centrifugation at 50,000×g in a Beckman TLA 100.4 rotor for 30 min at 4° C. After protein determination, samples are assayed for FMRP using the LUMINEX® capture ELISA as described above.

The capture ELISA method of the present invention allows for detection and quantification of a low abundant intracellular non-enzymatic protein in DBS. Thus, the invention can be applied in the detection and quantification of other relevant intracellular proteins by developing specific-ad hoc-capture immunoassays. Compared to conventional tests, the present invention has a very high signal to background ratio, works with BSA as blocking buffer which is used in all steps (before, during and after the capture step), has few and shorter incubation times (about 4 hours with the capture mAb, overnight with the detecting rabbit Ab, and the 2 hours with the anti-rabbit IgG Ab conjugated to phycoerythrin).Thus this assay can be performed in 24 hours and uses replenishable, specific, high-affinity anti-FMRP mAbs. Furthermore, the present invention may be used with the Luminex platform that allows for multiplex formats and several anti-FMRP mAbs can be used to detect FMRP in the same sample. Multiplex can be also performed with microsphere sets coupled with mAbs against other antigens. Multiplex assays can also be used as negative controls, or to detect diverse antigens for sample normalization.

The present invention is particularly valuable as it allows for detection and quantification of FMRP in the minute amount of proteins extracted from dried blood. The ELISA can identify male FM FX, male mosaic FM FX, from normal and from PM individuals (see FIG. 6). In as much as newborn DBS acquisition and screening for metabolic abnormalities is performed routinely in most of the U.S., and in a large number of countries in Europe, Americas and Australia, the present invention offers for the first time a valuable, simple, economical and accurate method to perform worldwide newborn screening for FXS in the general population.

Furthermore, the present invention provides a method that, for the first time, can detect and quantify low abundance intracellular non-enzymatic proteins in DBS by capture immunoassays. Therefore, the present invention can be applied in the diagnostic detection and quantification of other relevant intracellular proteins present in other neurodegenerative diseases. like the Batten Cln3 protein, which is not present in 85 percent of Batten Disease patients. The present invention can also be used to quantify FMRP in human chorionic villi and other organs and tissues, as well as to study FMRP expression at different stages of development.

EXAMPLE 6

The recombinant fusion protein for FMRP quantification was developed as part of this invention A glutathione S-transferase (GST) fusion protein carrying two short domains of FMRP corresponding to the epitopes of mAb6B8 and R477 was constructed with a double stranded synthetic oligomer encoding a nine amino acid sequence of FMRP (aa 344 to 352) that includes the epitope recognized by mAb6B8. The double stranded product, which was flanked by a 5' BamHI overhang and a 3' EcoRI overhang was ligated into vector pGEX-4T (GE Healthcare Biosciences, Piscataway, N.J.).

This plasmid, which expressed a peptide recognized by 6B8, was modified to include the R477 epitope as follows. The FMR1 cDNA region that encodes the R477 epitope was amplified with forward and reverse primers CGGAATTC-CGTGGAGGAGGCTTCAA (SEQ. ID NO. 4), CCCTC-GAGCAGCCGACTACCTTCCACTG (SEQ. ID NO. 5) and ligated the amplimer downstream of the 6B8 epitope to generate the plasmid pGEX-hFMR1-S. Clones were screened by western blot analysis for expression of a fusion protein, GST-SR7, that reacted with both antibodies. The fusion protein was expressed in *E. coli* strain BL21 by IPTG induction and purified by glutathione-Superflow resin (Clontech) according to the manufacturer's directions. After elution with 10 mM glutathione in 0.1M Tris-HCl pH 8.0 solution, GST-SR7 was dialyzed against 25 mM Tris-HCl pH 7.4, 150 mM NaCl buffer, concentrated in an Amicon Ultra-15 10K (Millipore), aliquoted, lyophilized and stored at −70° C.

The FMRP concentration was determined with serial dilutions of the recombinant fusion protein GST-SR7 (FIG. 16) to generate a standard curve for each plate using the MasterPlex QT v2.5 quantitative analysis software for protein assay (MiraiBio, Hitachi Solutions America Ltd, South San Francisco, Calif.). Median fluorescence intensity (MFI) was plotted against recombinant FMRP concentrations using a sigmoidal five parameter logistic model.

A Western blot analysis (FIG. 14) with protein samples (15 ug) analyzed on precast 4%-15% polyacrylamide Criterion Tris-HCl gels (BioRad, Hercules, Calif.) at 200 mV for 1 hr according to the manufacturer's directions. Separated proteins were transferred onto PVDF membranes (0.22 um, Bio-Rad, Hercules, Calif.) in transfer buffer (25 mM Tris, 192 mM glycine, pH 8.3) using a semidry electroblotter (OWL HEP-1, Thermo Scientific, Waltham, Mass.) for 1 hr at 10 V. Membranes were incubated in 5% nonfat dry milk in 0.01 M Tris pH 7.5; 0.137 M NaCl; 0.05% Tween 20 (blocking buffer) and then incubated with either anti-FMRP antibodies (mAb6B8, R477, or mAb 1C3 from EMD Millipore, Billerica, Mass.), or a rabbit anti-glyceraldehyde 3-phosphate dehydrogenase (0.2 ug/ml, sc-25778, Santa Cruz Biotechnology, Inc. Santa Cruz, Calif.). After washing, membranes were incubated for 1 hr with the conspecific alkaline phosphatase-conjugated secondary antibodies (Sigma-Aldrich Corp., St. Louis, Mo.). Proteins were detected with CDP-Star (NEB, Ipswich, Mass.) according to the manufacturer's directions.

The fragile X analysis of DNA isolated from blood samples (FIG. 22) was performed by PCR and Southern blot with the AmplideX® FMR1 PCR (RUO) reagents and capillary electrophoresis according to the manufacturer's directions (Asuragen, Austin, Tex. 78744 USA). DBS DNA was isolated with the DNeasy kit (Qiagen, Valencia, Calif.) according to the manufacturer's directions for QIAamp DNA Mini Kit, concentrated by precipitation with ethanol and analyzed with AmplideX® FMR1 PCR (RUO) reagents as above.

DBS from blood received more than 3 days after collection were excluded from the analysis. The single newborn blood sample DBS was also excluded. Data were analyzed with either SPSS (Chicago, Ill.) or SigmaPlot (Systat Software Inc., San Jose, Calif.) software.

Figure 14:
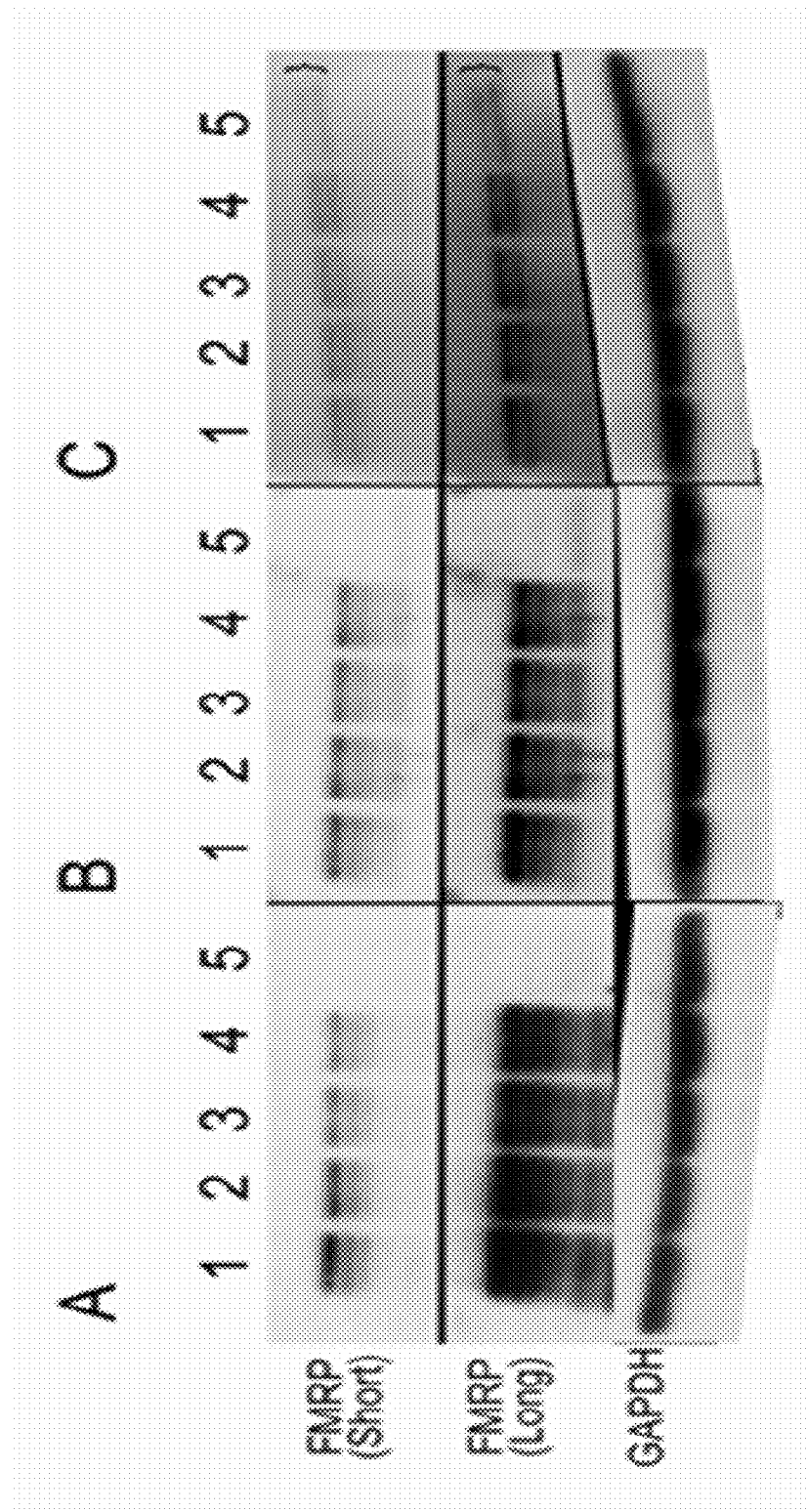

As described above, initial experiments suggested that mouse monoclonal antibody (mAb) 6B8 and rabbit polyclonal R477 that had been developed in accordance with the present invention were the best candidate pair. The specificity of mAb6B8 and R477 for FMRP seen in FIG. 14 was characterized by western blot analysis of extracts from normal (male and female), premutation (female), and full mutation (male) lymphocytes. Three major FMRP bands (68 to 80 kDa) were recognized by mAb6B8 in normal and premutation samples while no bands were detected by this antibody in the full mutation FXS male sample. This indicated that this antibody has little if any cross reactivity with the closely related proteins FXR1P and FXR2P or other unidentified proteins. Three bands (66-80 kDa) were detected with R477 in all extracts except male full mutation FXS. As seen in FIG. 14, this antibody also detected a faint band (65 kDa) in all lanes (normal, premutation and male FXS), that was visible on long exposure, indicating that R477 has a weak cross reactivity to an unspecified protein. Since the western blot data indicated that these antibodies both recognize FMRP without having any other targets in common, the combination of mAb6B8 and R477 as capture and detection reagents, respectively, should allow highly specific detection of FMRP in a capture immunoassay.

As illustrated in FIG. 4, the levels of FMRP detected (MFI) in the in normal cells were strictly proportional to the amount of sample. Background fluorescence values were detected in all wells containing male full mutation extracts, independently of the amount of sample tested. In normal individuals, N1 to N8 in FIG. 5, FMRP levels vary from 691 MFI and 1060 MFI. Similar values were measured in 4 premutation males (901 MFI to 1450 MFI). While background fluorescence was detected in a FM cell line (FM, 35 MFI), low amount of FMRP was found in a cell lines derived from two males full mutation mosaic (FM mos 1, 97 MFI, mos 2, 331 MF).

For FMRP quantification, as well as to control for technical variations in capture and detection, a reference protein was constructed for the LUMINEX® immunoassay. Referring to FIG. 15, a series of GST-fusion proteins were used that carry discrete regions of FMRP to localize the mAb6B8 and R477 epitopes (LaFauci et al.; manuscript in preparation) and a GST fusion protein was constructed, GST-SR7, that harbored both of them. Purified GST-SR7 at concentrations of 0.5 to 300 pM resulted in a linear response in the LUMINEX® assay (see FIG. 16). Repeated assays (55) of GST-SR7 at different concentrations were highly correlated (r=0.996) and long term (4 month) storage of the protein standard at −70° C. did not affect its performance which indicated that this standard was stable and not prone to aggregation.

Referring to FIG. 16, a standard curve calculated from dilutions of a known amount of GST-SR7 was used to measure the amount of FMRP present in DBS samples from 215 individuals with normal, premutation, or fragile X full mutation genotypes. Table 4 below shows the capture immunoassay quantification of FMRP in DBS extracts derived from normal, premutation and Full-mutation individuals.

TABLE 4

| Genotype | N | mean pM | median pM | Std. dev | minimum pM | maximum pM | Range |
| --- | --- | --- | --- | --- | --- | --- | --- |
| Females | | | | | | | |
| normal | 49 | 25.96 | 25.40 | 8.60 | 11.61 | 46.29 | 34.69 |
| Premutation | 59 | 22.99 | 22.49 | 7.01 | 9.86 | 38.73 | 28.87 |
| Full-mutation | 5 | 17.24 | 16.74 | 2.04 | 15.41 | 20.08 | 4.67 |
| Total females | 113 | | | | | | |
| Males | | | | | | | |
| normal | 85 | 25.80 | 24.79 | 10.30 | 8.61 | 51.49 | 42.88 |
| Full-mutation | 10 | 0.55 | 0.5 | 0.26 | 0.2 | 1.15 | 0.95 |

TABLE 4-continued

| Genotype | N | mean pM | median pM | Std. dev | minimum pM | maximum pM | Range |
|---|---|---|---|---|---|---|---|
| FM mosaic | 7 | 3.29 | 2.90 | 1.61 | 1.84 | 6.58 | 4.74 |
| Total FM | 17 | 1.70 | 0.72 | 1.71 | 0.20 | 6.58 | 6.39 |
| Total males | 102 | | | | | | |
| Total | 215 | | | | | | |

FMRP levels are reported as concentration (pM) in the 50 ul extracts which are equivalent to 8.7 ul of whole blood. As with lymphocytes, duplicate extracts of 57 DBS were highly correlated (r=0.96), indicating that the assay is also very reliable with these extracts. Referring to FIG. 17, on individuals with normal FMR1 alleles, the FMRP level appears to be normally distributed, with no difference between males and females. Moreover, the levels of FMRP followed a normal distribution in the group composed by both normal and premutation individuals. Referring to FIG. 18 the level of FMRP detected in the assay declines with age from infants to pre-teens and then appears to level off in teen years and remain unchanged through adulthood.

In males with a full mutation allele, the mean FMRP level was 1.7 pM (6% of normal) with a maximum of 6.6 pM (26% of normal). There was no overlap between full mutation and normal levels, as seen in FIG. 19A, and the difference between the two groups was highly significant (Mann-Whitney $p<0.001$). ROC analysis showed that, at a cut off of 7.59 pM, sensitivity and specificity were both 100% which indicates that the likelihood of false negative and false positive results using this LUMINEX® assay is extremely low. The full mutation male samples included full mutation mosaics which have a significantly higher level of FMRP, as seen in FIG. 19B ($p=0.001$). ROC analysis showed that, at a cut off of 1.5 pM, sensitivity and specificity were both 100% which indicates that this assay can distinguish mosaic fragile X from non-mosaic. Referring to FIG. 20, the level of FMRP detected in the LUMINEX® assay is consistent with the intensity of the premutation band in the Southern blot analysis of 2 mosaic full mutation males.

In females with a premutation allele, the mean FMRP level appeared to be lower than normal but the difference did not reach significance ($p=0.09$). The sample population included too few premutation males (2) to distinguish this group from the normal population. Although there were only 5 full mutation females in the sample population, this group was significantly different from normal allele females (Mann-Whitney, $p=0.032$), and from the combined group of females with either normal or premutation alleles (Mann-Whitney, $p=0.03$), as seen in FIG. 21.

The LUMINEX®-based capture immunoassay according to the present invention readily identified 14 male Fragile X full-mutation samples among DBS from 215 individuals with normal, premutation and full mutation alleles. The identification was accurate and in all cases matched the Fragile X genotype determined by Southern blot and PCR. The assay uses a new developed monoclonal antibody, mAb6B8 as capturing antibody, which has a high affinity for FMRP and detected no other proteins in western blots of lymphocytes extracts, as seen in FIG. 14. The new developed rabbit polyclonal antibody, R477, the detection antibody, also has high affinity for FMRP. In over-exposed western blots, however, R477 showed a very low cross-reactivity to an unidentified protein (lane 5). This protein is not recognized by mAb 6B8. Since only proteins recognized by both antibodies are detected in the capture immunoassay, the combination of mAb6B8 and R477 confers high sensitivity and specificity, and allows reliable measurements of FMRP in DBS punches derived from blood volumes as low as 2.2 ul (3-mm-diameter punch).

The assay of the present invention allows a low cost, rapid and direct quantitative measurement of FMRP that is specific, sensitive, and amenable to high throughput analysis for detection of full mutation FXS and suitable for screening of high-risk population and newborn.

What is claimed is:

1. A method of detecting a fragile X mental retardation protein in a human tissue sample, comprising the steps of:
   providing a first antibody that is coupled to a substrate, wherein said first antibody recognizes the epitope consisting of SEQ. ID NO. 3;
   exposing said first antibody to a human tissue sample;
   introducing a second antibody that is coupled to a fluorescent compound, wherein said second antibody recognizes a second epitope of the fragile X mental retardation protein;
   detecting whether said first and second antibodies have bound to any fragile X mental retardation protein in the human tissue sample, thereby detecting the fragile X mental retardation protein.

2. The method of claim 1, wherein the second epitope is SEQ. ID NO. 1.

3. The method of claim 1, wherein the first antibody does not have an affinity for fragile X related protein number one or fragile X related protein number two.

4. The method of claim 3, wherein the second antibody does not have an affinity for fragile X related protein number one or fragile X related protein number two.

* * * * *

SEQUENCE LISTING

<160> NUMBER OF SEQ ID NOS: 5

<210> SEQ ID NO 1
<211> LENGTH: 17
<212> TYPE: PRT
<213> ORGANISM: Homo sapiens

<400> SEQUENCE: 1

Asp Asp His Ser Arg Thr Asp Asn Arg Pro Arg Asn Pro Arg Glu Ala
1               5                   10                  15

Lys

<210> SEQ ID NO 2
<211> LENGTH: 9
<212> TYPE: PRT
<213> ORGANISM: Homo sapiens

-continued

```
<400> SEQUENCE: 2

Gly Pro Asn Ala Ser Pro Ser Glu Glu
1               5

<210> SEQ ID NO 3
<211> LENGTH: 6
<212> TYPE: PRT
<213> ORGANISM: Homo sapiens

<400> SEQUENCE: 3

Ser Arg Val Gly Pro Asn
1               5

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cggaattccg tggaggaggc ttcaa                                        25

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
ccctcgagca gccgactacc ttccactg                                     28
```